(12) United States Patent
Chamberlin et al.

(10) Patent No.: US 7,619,734 B2
(45) Date of Patent: Nov. 17, 2009

(54) METHODS AND SYSTEMS FOR COMPUTING A SIZE DISTRIBUTION OF SMALL PARTICLES

(75) Inventors: Danielle R. Chamberlin, Belmont, CA (US); William R. Trutna, Jr., Atherton, CA (US); Maozi Liu, Fremont, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 20 days.

(21) Appl. No.: 12/082,773

(22) Filed: Apr. 14, 2008

(65) Prior Publication Data
US 2009/0219528 A1    Sep. 3, 2009

Related U.S. Application Data

(60) Provisional application No. 61/068,101, filed on Mar. 3, 2008, provisional application No. 61/068,098, filed on Mar. 3, 2008.

(51) Int. Cl.
*G01N 15/02* (2006.01)
*G01N 21/00* (2006.01)

(52) U.S. Cl. ....................... 356/335; 356/432
(58) Field of Classification Search .......... 356/335–344
See application file for complete search history.

(56) References Cited

U.S. PATENT DOCUMENTS

| | | | | |
|---|---|---|---|---|
| 3,499,159 | A | * | 3/1970 | Lee et al. .................. 250/564 |
| 3,700,333 | A | * | 10/1972 | Charlson et al. ............ 356/339 |
| 4,154,089 | A | * | 5/1979 | Carlon .................... 73/29.01 |
| 5,121,629 | A | * | 6/1992 | Alba ..................... 73/61.41 |
| 5,438,408 | A | * | 8/1995 | Weichert et al. ........... 356/336 |
| 5,818,583 | A | * | 10/1998 | Sevick-Muraca et al. .... 356/336 |
| 6,119,510 | A | * | 9/2000 | Carasso et al. ............ 73/61.75 |
| 7,257,518 | B2 | | 8/2007 | Alba |

OTHER PUBLICATIONS

Bohren et al., Absorption and Scattering of Light by Small particles, pp. 316-318, 1983.
Thiele et al., Light-Scattering of Representative, Morphological Rutile Titania Particles Studied Using a Finite-Element Method, pp. 469-479, vol. 81, No. 3, Mar. 1998.

* cited by examiner

*Primary Examiner*—Gregory J Toatley, Jr.
*Assistant Examiner*—Jarreas C. Underwood

(57) ABSTRACT

Methods, systems and computer readable media for computing small particle size distributions. A reference matrix of pre-computed reference vectors is provided, with each reference vector representing a discrete particle size or particle size range of a particle size distribution of particles contained in a dilute colloid. A measurement vector of measured extinction values of a sample dilute colloid is provided, wherein the measured extinction values have been measured by spectrophotometric measurement at the discrete wavelengths. Size distribution and concentrations of particles in the sample dilute colloid are determined using linear equations, the reference matrix and the reference vector.

27 Claims, 15 Drawing Sheets

Comparison of Fit to 300 nm and to 1 micron Polystyrene

METHODS AND SYSTEMS FOR COMPUTING A SIZE DISTRIBUTION OF SMALL PARTICLES

CROSS-REFERENCE

The application claims the benefit of U.S. Provisional Application No. 61/068,101, filed Mar. 3, 2008 and U.S. Provisional Application No. 61/068,098, filed Mar. 3, 2008, both of which are hereby incorporated herein, in their entireties, by reference thereto and to which we applications we claim priority under 35U.S.C. Section 119.

BACKGROUND OF THE INVENTION

Many industrial processes involve the manufacture of particles and the properties of the item of manufacture (pharmaceuticals, paint, food, chemicals, etc) depend heavily on the size of the particles used. Oftentimes these processes involve mixtures of particles, such as a mixture of particles of one material having more than one particle size or a mixture of particles of more than one material wherein the mixture includes more than one particle size. However, current particle sizing techniques do not generally distinguish between the different sizes of particles in a given particle size distribution and report a "universal" particle size distribution for all particles present in a sample. If a feature is observed, for example a peak due to fine particles, it is not known which constituent of a mixture contributes to that particular particle size.

Some current techniques for measuring particle size distributions for small particles, such as Dynamic Light Scattering, rely upon the Brownian motion of the particles to derive estimates of their size measurements. However, computations of size estimates can take several minutes and these techniques are therefore not ideal for online processes. Further, when the particles are not monodisperse (i.e., all of substantially one size), signals measured from movements of the larger particles can tend to blur signals measured from movements of the smaller particles to the extent that the smaller particles are not properly measured, or not even detected at all.

U.S. Pat. No. 5,121,629 discloses a method for measuring particle size distribution and concentration based on directing ultrasonic waves through a suspension of particles in a suspending medium. Size distribution and concentration calculations include fitting two lognormal distributions to the measurements, based on the assumption that the particle size distribution is the sum of two lognormal distributions. There is no basis for this assumption and it sometimes leads to incorrect solutions. The Powell Discriminator described can erroneously lead to a local minimum solution that is not the overall global minimum solution and is therefore the wrong solution. Also, these calculations are not fast, taking on the order of thirty minutes to calculate particle size distribution and concentration values for a single measurement.

U.S. Pat. No. 7,257,518 discloses a method of calculating particle size distributions and concentrations of particles that are densely concentrated, so that multiple scattering effects must be accounted for. This method relies upon nonlinear methods of estimating the particle size distribution and concentrations and can take a considerable amount of time to calculate measurement estimates.

Some existing particle size distribution estimation methods provide plots of estimates that are unacceptably noisy (e.g., spiky). There is a need for improved methods for providing estimations that are smoothed and therefore provide more definite values for a distribution and values that can be more readily read and ascertained by a user.

There is a continuing need for fast and accurate methods of measuring size distribution of small particles, particularly for use in online applications, for real time or near-real time calculations of measurements during performance of a process where small particles are employed. Even for offline applications, it would be desirable to provide faster, accurate methods of measuring particle size distributions.

BRIEF DESCRIPTION OF THE DRAWINGS

FIG. 9B also shows the plot of FIG. 9A for comparison purposes.

DETAILED DESCRIPTION OF THE INVENTION

Figure 1:
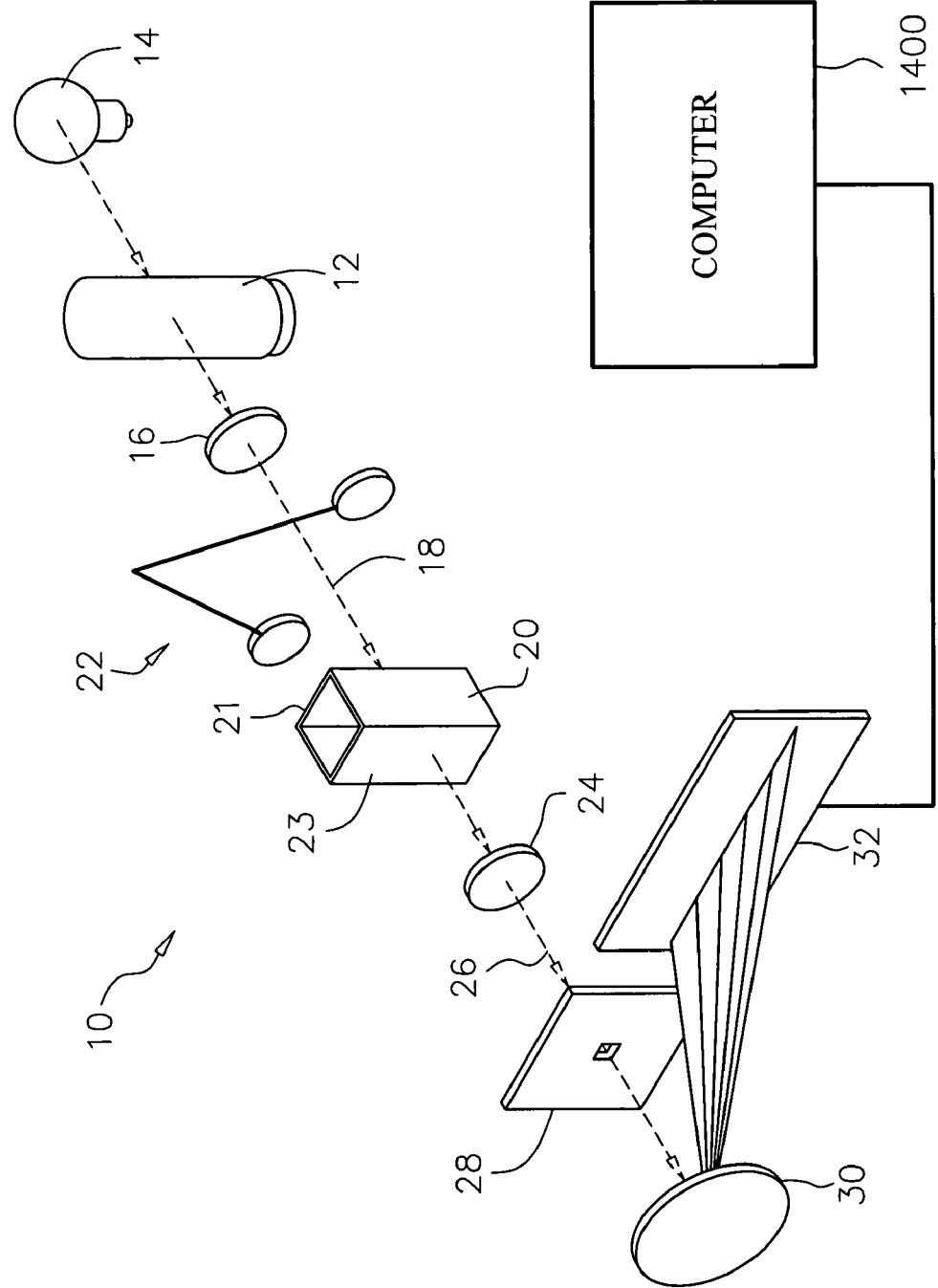
FIG. 1 is a schematic diagram of a spectrophotometer that may be used to measure scattering spectra of particles by spectrophotometry.

Before the present methods, systems and computer readable media are described, it is to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a vector" includes a plurality of such vectors and reference to "the particle size" includes reference to one or more particle sizes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "monodisperse" refers to a sample containing particles wherein all of the particles contained are of substantially the same size.

The term "polydisperse" refers to a sample containing particles that include a distribution of various particle sizes.

A "dispersion" refers to solid particles in a liquid.

An "aerosol" refers to solid and/or liquid particles in a gas.

An "emulsion" refers to liquid droplets in another liquid.

A "colloid" refers to particles in any phase in any fluid.

A "dilute" colloid refers to a colloid having a volume percentage of particles that is less than a volume percentage effective to produce significant multiple scattering when the attenuation spectrum of the particles is measured. Accordingly, multiple scattering effects do not need to be accounted for when measuring the attenuation spectra of a dilute colloid. In at least one embodiment, a dilute colloid is defined as one having particles in an amount less than about 1% by volume.

"Flowing" means that there is relative motion between particles and the interrogating light beam, over and above relative motion due to Brownian motion.

"Particle size" measurements refer to the diameter or largest cross sectional dimension of a particle. Particles are assumed to be roughly spherical in cross-section. In practice, the term "particle size" refers to a small range of particle sizes.

A "particle size distribution" (occasionally abbreviated as "PSD") refers to a characterization of the various particle sizes that are present in a colloid, and the relative concentrations of each. The particle size distribution can be represented by a histogram. Each bin in the histogram refers to a small range of particle sizes displayed as the x-axis of a plot. The number of particles in each size bin is displayed on the y-axis. Additionally, the number of particles is weighted by the volume of the average particle in the bin. The y-axis of the plot represents the volume fraction of the particles in the bin. The total volume of particles in a unit volume of colloid is the sum of the volume fraction in each of the bins. Ideally the histogram is plotted as a bar graph, which represents the width of the bins, but only the height of the bars is plotted against the mean bin size as a two dimensional plot.

A "concentration" of particles refers to the volume occupied by particles in a unit volume of colloid.

A "wavelength" refers to the distance, measured in the direction of propagation of a wave, between two successive points in the wave that are characterized by the same phase of oscillation.

The term "on line" refers to measurement of a process with automated sampling and sample transfer to an automated analyzer.

The term "in line" refers to measurement of a process where the sample interface is located in the process stream.

The term "at line" refers to measurement of a process involving manual sampling with local transport to an analyzer located in the manufacturing area.

The term "small particles" as used herein, refers to particles within a range of about 5 nm to about 50 µm or to any subrange of this size range.

Embodiments of the present invention determine a particle size distribution for a sample of small particles by comparing a measurement vector and a reference matrix composed of reference vectors. The measurement vector represents the measured extinction spectrum of a dilute colloid composed of the sample particles dispersed in a fluid. The reference vectors each represent the extinction spectrum of a reference dilute colloid composed of particles of the same particle material as the particles of the sample and having a respective single particle size. The reference vectors are typically pre-computed, but may alternatively be obtained empirically or experimentally.

The particles in the dilute sample colloid may be in the solid, liquid, or gaseous (vapor) phase, and the medium they are dispersed in may be in the solid, liquid or gaseous (vapor) phase. The particles may be any material for which the complex refractive index is known or can be measured over the ultraviolet (UV) to near infrared (NIR) wavelength range. The range of solid particles which can be measured includes ceramics, metals, and polymers. The range of colloids from which particles can be measured includes dispersions, aerosols and emulsions. Exemplary fluids include liquids and gases, including, but not limited to: water, air, alcohols, solvents, oils, or any other liquid or vapor.

When a broad particle size distribution is present, post-processing is performed to remove noise generated by large particle sizes. In any case, smoothing of results can be applied to smooth out spikiness that may be present in a particle size distribution due to artifacts of the inversion algorithm.

Mie Scattering

Embodiments of this invention include methods for efficiently and quickly computing the particle size distribution of a sample of small particles using linear equations, the measurement vector and the reference matrix. The extinction spectra represented by the measurement vector and reference matrix are essentially Mie scattering spectra. Bohren and Huffman, *Absorption and Scattering of Light by Small Particles*, Wiley-VCH, 1983, pp. 318-319, which is hereby incorporated herein, by reference thereto, describe the basic theory of Mie scattering and how it can be used to measure the particle size of particles in a monodisperse sample.

FIG. 1 is a schematic diagram of a spectrophotometer 10 that may be used to measure the extinction spectrum of a dilute colloid comprising a sample of small particles by spectrophotometry. One non-limiting example of a spectrophotometer that may be employed for such purposes is the Agilent 8453 UV/Visible Spectrophotometer (Agilent Technologies, Inc., Santa Clara, Calif.). In this example, spectrophotometer 10 includes a light source that incorporates both an ultraviolet light source 12, such as a deuterium arc lamp, and a near-infrared-visible light source 14, such as a tungsten lamp. By using two different light sources generating light in different wavelength ranges, the smaller-sized particles in a particle size distribution scatter more in the shorter wavelength light (UV spectrum) more while the larger-sized particles in the particle size distribution scatter the longer-wavelength light (near-IR—visible) more. This differential scattering is effectively wavelength division multiplexing, so that the spectra due to the smaller-sized particles are distinguished from the spectra due to the larger-sized particles by the shorter-wavelength extinction spectrum and the longer-wavelength extinction spectrum that are generated. Optics 16 collimate the light received from sources 12 and 14 into a beam 18 that is focused onto a sample, which, in the example shown, is contained in a sample cell 20. A shutter mechanism 22 may be provided which is actuatable to control whether the beam 18 is incident on the sample or is prevented therefrom. In one example, sample cell 20 is a cuvette having plane parallel faces 21 and 23 formed of polished, fused quartz.

Additional optics 24 are provided on the output side of the sample cell 20 to direct an output beam 26 of light that is transmitted through the sample to slit 28. Light that passes through slit 28 is reflected off grating 30, which spreads beam 26 into its constituent wavelength components that are detected by a photodiode array 32. In the Agilent 8453 UV/Visible Spectrophotometer, the photodiode array is composed of 1024 photodiodes. Other array detectors may be alternatively used, such as, but not limited to a charge-coupled device (CCD) or complementary metal-oxide semiconductor (CMOS) detector. Alternatively, a spectrophotometer 10 may not employ the photodiode array 32, but rather, scan the output light 26 with a single detector by rotating the grating 30 to enable the single detector to detect various wavelengths in the wavelength range of the output light 26. However, use of the photodiode array 32 is preferred because it is faster.

A sample dilute colloid is formed from a sample of small particles (e.g., within a range of about 5 nm to about 50 µm) in a suitable fluid (e.g., water, air, oils, alcohols, solvents, etc.). The sample dilute colloid is put in the sample cell 20 to be analyzed. Analysis of static samples of particles in a liquid or gas can be analyzed. For analysis of small particles in a liquid, sample cell 20 may alternatively comprises a flow-through cell. For analysis of small particles in a gas, a stream of the sample dilute colloid may be flowed into the sample cell 20. Alternatively, for analysis of small particles in a gas such as an aerosol, the aerosol can be flowed through the open space in the system 12 between the light sources 10, 12 and the detector 32, e.g., in the space occupied by the cell 20 in FIG. 1, as the cell 20 can be removed in this case. Alternatively to measuring particles in a flowing stream, measurements of a batch process can be performed, wherein samples are taken from the batch process and measured at line. An extinction spectrum of the (or each, in the case of batch processing) sample colloid is measured with the spectrophotometer 10. Collimated light 18 passes through the sample cell 20, where the sample colloid attenuates the light by scattering and absorption. The remaining light 26 is spectrally dispersed by diffraction grating 30 onto photodiode array 32, which converts light intensity to an electrical signal that is representative of the extinction spectrum of the sample colloid. The electrical signal is processed to calculate the particle size distribution of the sample particles. The measured extinction spectrum is represented by a measurement vector that can then be used to determine the particle size distribution of the sample particles, as will be described below.

The Mie scattering theory (Gustav Mie, 1908) for a dilute colloid comprising spherical particles provides a means to calculate the scattering component and the absorption component of the extinction spectrum of a dilute colloid in which the volume concentration of the particles in the colloid, the particle radius a, the length of the cell containing the colloid, the particle refractive index, and the fluid refractive index are all known. The Mie scattering theory computes two quantities, the absorption cross-section $C_{abs}$ and the scattering cross-section $C_{sca}$. These cross sections add together to produce a third quantity $C_{ext}$, the extinction cross-section. The extinction spectrum referred to herein is the extinction cross-section at each of a number of wavelengths in a range of wavelengths. All three cross sections have units of area and represent the effective cross-sectional area of the scattering, absorbing or scattering and absorbing sphere. Light that is lost to scattering is lost by radiation in directions that are outside the range of angles of the light that the spectrophotometer is capable of measuring. Light that is absorbed is captured by the particles and ultimately gets turned into heat. Particles that are transparent at a particular wavelength, such as silica particles, have a zero absorption cross-section at that wavelength. In the present invention, the extinction cross section $C_{ext}$ is used, as it is irrelevant by what means the light is lost during the measurement.

The "relative cross section" is the extinction cross-section divided by the physical area of the spherical particle, and is defined mathematically by:

$$Q_{est} = \frac{C_{ext}}{\pi a^2} \quad (1)$$

where a is the particle radius. $Q_{ext}$ is a unitless quantity that is a measure of the extinction efficiency. The present invention does not distinguish between light that is lost by absorption and light that is lost by scattering, but only measures extinction. If $Q_{ext}$ is less than 1, then the apparent size of the particle is less than its physical size.

As long as the sample colloid comprising the sample particles is dilute (so that multiple scattering effects do not need to be considered in the calculations) then the transmittance of a cell 20 (power out divided by the power in) containing a sample colloid having a particle density of N particles per unit volume is:

$$T = e^{-\alpha L} \quad (2)$$

where $\alpha = NC_{ext}$ and L is the cell length. The spectrophotometer 10 measures attenuation, which is the negative logarithm of the transmittance, expressed as:

$$AU = \alpha L \times \text{Log}_{10} e = NC_{ext} \text{Log}_{10} e \times L \quad (3)$$

where AU stands for absorbance units, the numbers computed by the spectrophotometer. The particle density N can be expressed in terms of a volume fraction $C_v$, wherein the number of particles per unit volume times the volume of a single particle is the volume fraction occupied by the particles. This is expressed mathematically in the following way:

$$C_v = \frac{4}{3}\pi a^3 N \quad (4)$$

In other words, the number of particles N per unit volume times the volume $(4/3\pi a^3)$ of a single particle is the fraction of the volume $C_v$ occupied by the particles.

Combining equations (1), (3), and (4) gives an expression for the attenuation per unit length:

$$\frac{AU}{L} = \frac{3\text{Log}_{10} e}{4a} C_v Q_{ext} = \frac{3\text{Log}_{10} e}{4a} C_v (Q_{sca} + Q_{abs}) \quad (5)$$

where $Q_{sca}$ is a unitless quantity that is a measure of the scattering efficiency and $Q_{abs}$ is a unitless quantity that is a measure of the absorption efficiency.

Equation (5) can be used to compute optical attenuation from the extinction cross-section obtained from the Mie calculation. The present invention provides solutions for computing the particle size distribution from the measured extinction spectrum. That is, the particle size distribution can be computed using the measured extinction spectrum as an input. This problem belongs to a class of problems known as "inverse problems", which are notoriously difficult to solve. The present invention uses any of several linear programming methods to solve this problem.

Before the inverse problem is described, equation (6) first mathematically describes how the extinction spectrum of particles in a dilute colloid can be calculated using a matrix M of reference vectors and a concentration vector. A matrix equation of the form of equation (6) below can be used to calculate the extinction spectrum of a dilute colloid composed of a given fluid and given particles having a given particle size distribution. The particle size distribution is composed of a discrete set of particle sizes a, with a different particle concentration (volume concentration) for each particle size:

$$M \cdot c = s \quad (6)$$

where M is a matrix containing the reference vectors (see the right hand side of equation (8) below), one for each particle size or small range of particle sizes, c is a column vector composed of a respective particle concentration for each particle size in the range of particle sizes, and s is the computed extinction spectrum, also a column vector. That is, the calculated extinction spectrum is composed of a calculated extinction for each wavelength in the range of wavelengths over which the calculation is performed. Each calculated extinction covers a different wavelength or range of wavelengths of the extinction spectrum.

The particle size distribution and particle concentrations can be determined from a measured extinction spectrum by linear methods, such as when the PSD and thus the concentration vector c are not known, and the extinction spectrum is measured and is represented by a measurement vector s. It is noted that the extinction cross-section is a function of particle radius, and particle and fluid refractive indices (refractive indices of the sample particles and fluid constituting the dilute colloid). Therefore equation (5) can be expressed in the following form:

$$\frac{AU}{L} = C_v f(a, n_p(\lambda), n_f(\lambda)) \quad (7)$$

Where $n_p$ and $n_f$ are the wavelength-dependent refractive indices of the particles and the fluid, respectively. For a discrete set of measurement wavelengths $[\lambda_1, \lambda_2, \lambda_3 \ldots \lambda_n]$ such as that of the spectrophotometer 10, equation (6) can be written as the product of a vector representing an extinction spectrum and a particle concentration, which is a scalar quantity.

$$[AU(\lambda_1), AU(\lambda_2), AU(\lambda_3) \ldots AU(\lambda_n)] = C_v L[f(a, \lambda_1), f(a, \lambda_2), f(a, f_3), \ldots f9a, \lambda_n)]( \quad (8)$$

where the function $f$ now implicitly includes the materials properties for a particular dilute colloid, i.e., the materials properties of the sample particles and the fluid that constitute the colloid.

Reference Matrix

The matrix M described above is referred to herein as a reference matrix, and includes columns of reference vectors. Each reference vector represents a reference extinction spectrum for a respective reference colloid. The respective reference colloid is composed of reference particles of the same particle material as the sample particles and having a respective single discrete particle size or small range of small particle sizes. The reference particles are dispersed in the same fluid as that which constitutes the fluid of the sample dilute colloid. In one embodiment, the reference extinction spectrum represented by each reference vector is composed of a wavelength value and an extinction value measured at that wavelength value by spectrophotometer 10 for a reference dilute colloid having the respective single particle size. In another embodiment, the reference extinction spectrum represented by each reference vector is composed of a wavelength value and an extinction value computed at that wavelength value for a reference dilute colloid having the respective single particle size. In embodiments in which the wavelength values are conveyed independently of the reference vectors, the wavelength values may be omitted from the reference vectors.

Using equation (8), the particle size distribution measurement problem can be expressed as:

$$\begin{bmatrix} m_{11} & m_{12} & m_{13} & \dots & m_{1m} \\ m_{21} & m_{22} & m_{23} & \dots & m_{2m} \\ m_{31} & m_{32} & m_{33} & \dots & m_{3m} \\ \vdots & \vdots & \vdots & \ddots & \vdots \\ m_{n1} & m_{n2} & m_{n3} & \dots & m_{nm} \end{bmatrix} \begin{bmatrix} c_1 \\ c_2 \\ c_3 \\ \vdots \\ c_m \end{bmatrix} = \begin{bmatrix} s_1 \\ s_2 \\ s_3 \\ \vdots \\ s_n \end{bmatrix} \quad (9)$$

where the measurement vector representing the measured extinction spectrum of the sample dilute colloid is substituted for the computed extinction spectrum s in equation (6). The concentration vector c is solved for to give the particle size distribution of the sample particles. The sample size distribution is composed of a particle concentration for each of the various particle sizes.

Various different approaches/algorithms can be used to solve for the concentration vector c, some having more drawbacks than others. One approach computes the inverse of M and then solves for c by multiplying the inverse of M by s. This approach works on the condition that the matrix M is a square non-singular matrix. In practice, this condition is typically not satisfied.

Other approaches attempt to find a concentration vector c that minimizes the least-square error in the fit error between the measurement vector and the extinction spectrum calculated using the reference matrix and concentration vector, as described in the following. As one example the pseudo-inverse of the matrix M is computed, and then c is solved for by multiplying the pseudo-inverse of M by s. This method is based on Singular Value Decomposition of matrix M. The advantages of this approach are that it does not require a square non-singular matrix. Although this works well in theory, in practice measurement errors, noise, and uncertainties in refractive indices renders this approach less than desirable, as it sometimes computes negative values for the concentrations in some size bins/particle sizes.

Another method uses the "NMinimize" routine in the MATHEMATICA® computer application (Wolfram Research). NMinimize is a numerical optimization routine that finds the concentration vector which minimizes the least square fit error in the computed spectrum using the Nelder Meade algorithm. Non-negative constraints are applied to the concentration vector elements. This allows equation (6) to be solved with constraints on the concentration vector c. The only constraint necessary is the requirement that the elements of the concentration vector c be non-negative.

Quadratic Programming is another approach that may be used. The quadratic programming technique is used in a similar fashion to the NMinimize algorithm, with the exception that it requires matrix M to be positive definite. While this condition is not true for matrix M in general, matrix M may be forced to be positive definite by altering the matrix M slightly. This method works, but altering the matrix M also alters the calculation results, and therefore this is not an ideal approach.

QR decomposition is the preferred approach to use with the present invention. In linear algebra, the QR decomposition (also called the QR factorization) of a matrix is a decomposition of the matrix into an orthogonal and a triangular matrix. The QR decomposition is often used to solve the linear least squares problem. The QR decomposition is also the basis for a particular eigenvalue algorithm, the QR algorithm. The QR decomposition is an intermediate step in solving the non-negative least squares problem solved by the methods described herein. QR decomposition can be implemented with positive concentration constraints on the concentration vector c. The measured spectrum vector and the reference matrix are inputted and the QR decomposition algorithm finds the optimum concentration vector with the constraints that concentrations are non-negative. The QR decomposition, NMinimize, and Quadratic programming are all used in similar ways, although the details of the methods are different. NMinimize is too slow and it is proprietary code. Quadratic programming distorts the result, as noted above. QR decomposition is the preferred option among these three. The only potential issue found when using QR decomposition is that it in some instances may tend to produce a narrower particle size distribution than is physically reasonable.

Other constrained least-squares solutions that may be used include, but are not limited to those identified in Golub, *Matrix Computations*, $3^{rd}$ edition (which is hereby incorporated herein, in its entirety, by reference thereto): Ridge Regression, Equality Constrained least squares, the method of weighting or LS minimization over a sphere.

Figure 2:
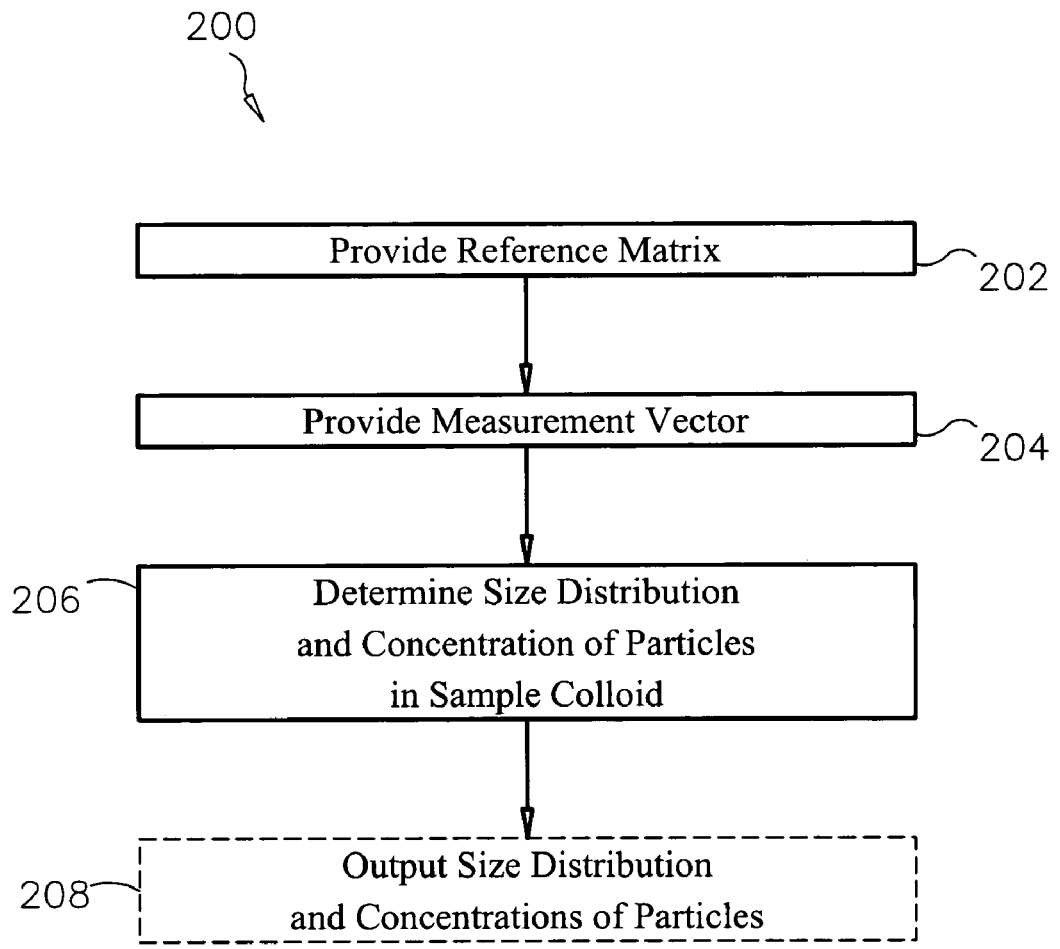
FIG. 2 is a flow diagram of a method for computing small particle size distributions according to an embodiment of the present invention.

FIG. 2 is a flow diagram 200 showing an example of a method for computing the particle size distribution of a sample of small particles according to an embodiment of the present invention. At 202 a reference matrix M of pre-computed or pre-measured reference vectors is provided, each reference vector representing a discrete particle size of a particle size distribution of particles contained in a reference colloid, each reference vector representing a reference extinction spectrum over a predetermined wavelength range.

Each reference vector (column) of the reference matrix M includes a reference extinction spectrum calculated or measured for a respective reference colloid comprising particles of a single, known particle size. The reference colloid is a dilute colloid of specified concentration. The reference particles are particles of a particle material having known values of refractive index at various wavelengths within the wavelength range over which the measure extinction spectrum is measured. Typically, but not necessarily, in each reference vector, each element is composed of a wavelength and an extinction value. The extinction value is calculated at the wavelength for the respective reference colloid or is measured at the wavelength by spectrophotometric measurement of the respective reference colloid.

At 204, a measurement vector representing measured extinction values of a sample colloid comprising the sample particles is provided. As noted above, the sample colloid is a dilute colloid. The particles in the sample colloid are the same material as some or all of the particles of the reference colloid (s) used to generate the reference matrix. The measured extinction values are those measured by spectrophotometric measurement at discrete wavelengths. The measurement of the sample dilute colloid may be performed online, in real time, with the spectrophotometer inputting the measurement vector into the system for calculation of particle size distribution. Because of the speed of these methods, particle size distribution and particle concentration calculations can be performed for sample particles that constitute part of a flowing sample colloid. The sample colloid may be obtained, for example, from a process stream. The spectral measurement used to provide the measurement vector is fast, on the order of a second, when using a spectrophotometer such as the Agilent 8453. The computation of the particle size distribution and particle concentrations from the measurement vector takes only a few additional seconds when using the fast matrix methods for linear least squares deconvolution described herein. Advantageously, this allows real time calculations of particle size distributions and particle concentrations. Such real time calculations can be performed for sample particles that constitute part of a static sample colloid, as well as for sample particles that constitute part of a flowing sample colloid. For example, the present methods can be performed iteratively to provide particle size distributions and particle concentrations that can be analyzed to measure crystal growth, or a reduction in the particle sizes of particles in a process stream, or in a still sample. These iterative calculations can be performed after every passing of a predetermined time interval, e.g., every five seconds, every two and a half seconds, or even every one second. Of course, other predetermined time intervals not mentioned here, and greater than one second can be set. If the measurement time of the spectrophotometer can be reduced, this would allow the present methods to be performed iteratively over a time interval of less than one second. The results of the calculations from multiple iterations can be compared with one another and/or against a predetermined threshold value that is meaningful to a process. For example, a chemical process may be designed to produce particles having a predetermined size. Accordingly, a threshold can be set for a predetermined concentration of particles at that predetermined size. When, upon comparing calculated particle size distribution and particle concentration results, or comparing the concentration of a particular particle size of interest only with a predetermined concentration threshold for that size (which can simplify and thus even further increase the calculation processing) the comparison identifies a particle concentration of the particle size of interest (predetermined size) that is equal to or greater than the predetermined concentration, than the process can be configured to generate an alert to indicate that the process has achieved a goal. Similar monitoring can be performed to identify when a process has reduced the sizes of particles to a predetermined particle size or to achieve a predetermined particle size distribution.

In one example, the extinction spectrum of a process stream is measured using, for example, a spectrophotometer 10. First an initial measurement is made of the extinction spectrum of the fluid component (that is, without the particles to be measured) of the colloid in the uv-NIR wavelength range. This measurement of a "blank" spectrum using a sample cell containing the fluid without the particles provides a reference attenuation of the medium component alone. It also calibrates the spectrophotometer to compensate for changes in the lamp spectra and the various losses and gain in the entire system. Next, the extinction spectrum of light transmitted through the sample dilute colloid containing the sample particles is measured in the same way that the initial measurement was made. The second measurement with particles gives an accurate measure of the excess attenuation due to the particles, according to the following. The resulting spectrum obtained by dividing the measured extinction spectrum of the sample colloid by the initial extinction spectrum represents wavelength-dependence of the total light-attenuating effect of all the sample particles in the path of collimated beam 18 (FIG. 1) through the sample colloid. The measured spectrum is represented by a measurement vector. This measurement vector is then deconvolved, such as by QR decomposition, using a least squares fit, such as a non-negative least squares (NNLS) fit, to minimize the difference between the measurement vector and the calculated extinction spectrum obtained from the concentration vector and the reference matrix M in a manner as described above. A particle size distribution vector is given by the concentration vector providing the best least-squares fit. The elements of the concentration vector can be used to give the particle concentration of each size of particle present in the sample.

That is, the particle size distribution and particle concentrations of the sample particles in the sample colloid are determined at 206, using linear equations, the reference matrix M and the measurement vector in a manner as described above. Of course, the present invention is not limited to providing the particle size distribution, as the present methods can be used to determine only the particle size, determine only the concentration of a particle size of interest, or to determine any subset of the information provided by the full particle size distribution with particle concentrations. Optionally, the particle size distribution and concentrations of particles in the sample colloid can be output at 208. Additionally or alternatively, further processing can be performed, including, but not limited to comparing one or more particle size distributions and/or one or more of the concentrations to a threshold value and/or to each other.

For example, if the sample particles in the sample colloid are known to be only particles of particle material "A", the reference extinction spectra for reference colloids respectively comprising particles of particle material "A" are computed or measured over a range of particle sizes of interest (e.g., a range of particle sizes within which the particle sizes of the sample particles are expected to lie) and the reference extinction spectra are included in the reference matrix M. Each reference colloid is a dilute colloid comprising particles having a known single particle size. The concentration vector given by the least-squares fit of the measurement vector to the extinction spectrum calculated using the reference matrix and concentration vector gives the particle concentration of each size of sample particle present in the sample.

Figure 3:
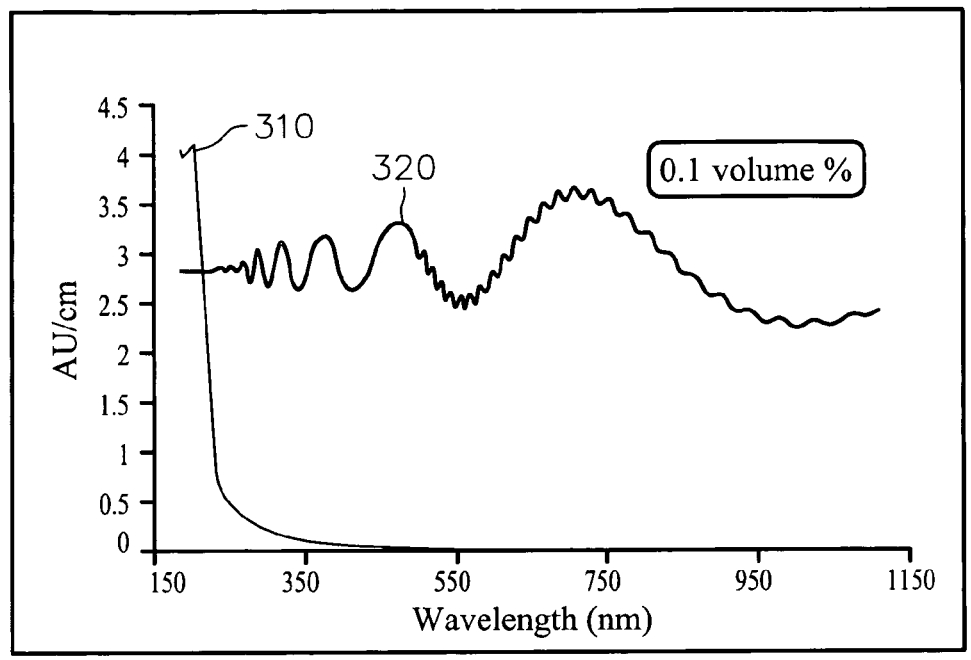
FIG. 3 shows the attenuation spectra of dilute colloids of polystyrene particles having sizes of about 100 nm and 5 μm at a concentration of about 0.1 volume percent, calculated over a wavelength range of about 190 nm to about 1100 nanometers.

Extinction spectra can vary drastically depending on the particle sizes of the particles measured. FIG. 3 shows at 310 and 320 the calculated extinction spectra of two exemplary sample colloids comprising polystyrene particles having particle sizes of about 100 nm and 5 μm, respectively, at a particle concentration of about 0.1 volume percent. The extinction spectra are calculated over a wavelength range of about 190 nm to about 1100 nanometers. The extinction spectra 310 and 320 have been overlaid in FIG. 5 for comparison purposes, but each was calculated separately.

Calculating the reference extinction spectra of monodisperse reference colloids each comprising particles of a single particle size is straightforward and each calculation produces a unique result. However, the inverse operation, as noted above, is not straightforward, i.e., the calculation of particle size distribution from a measured extinction spectrum does not necessarily result in a unique solution. For example, colloids having different combinations of different size particles can create the same measured extinction spectrum when measured, as spectral features tend to "wash out" when particles having large numbers of different particle sizes are present. Also, it is difficult to measure the particle size distribution of particles that are much smaller than the wavelengths used to measure the extinction spectrum, e.g., particles having a size approaching the Rayleigh scattering limit. The above-described method of computing particle size distribution is well-adapted to measuring particle sizes in the range of about 10 nm to about 15 μm. The above-described method provides the most probable solution to the calculation of the particle size distribution and particle concentration, by finding the particle size distribution whose extinction spectrum is the best least squares fit to the measured extinction spectrum.

When determining a reference matrix M, the range of particle sizes over which particles are expected to be present in the sample is divided into a number of discrete particle sizes. Each particle size covers a respective portion of the entire range of particle sizes over which the particle size distribution is to be measured. Typically this division will result in hundreds of particle sizes. Typically, the entire range of particle sizes is divided into particle sizes on a logarithmic scale.

For each particle size, the respective reference extinction spectrum is generated by computing or measuring a reference extinction value at each one of multiple discrete wavelengths over the range of wavelengths in which the measured extinction spectrum is measured. In an example, respective extinction values are measured or computed at wavelengths differing by 1 nm steps or differing by increments each of which is an integer multiple number of nanometers. In at least one embodiment, reference extinction spectra are computed or measured at wavelengths differing by increments of 4 nm, which gave an acceptable compromise between resolution and operational speed. Thus, there are also typically hundreds of rows in the reference matrix M, each corresponding to one wavelength. In equation (9) above, referring to the reference matrix M, n is the index number of the particle size, m is the index number of the wavelength at which the extinction value is measured, and each column of the matrix M represents a reference vector representing the reference extinction spectrum of a reference colloid comprising particles of a respective particular size.

After a measurement vector is provided, as described above with regard to FIG. 2, 204, the least squares error is calculated between the reference extinction spectrum (obtained by multiplying a value of concentration vector c by matrix M) and the measured extinction spectrum (represented by the measurement vector) and the least squares error is minimized by varying the calculated spectrum (e.g., by varying the values of the concentration vector c, and thereby finding the best fit solution where a global minimum in the least squares error results. An extinction spectrum is computed by multiplying the matrix M by the concentration vector. Then the process finds the concentration vector that minimizes the error between the measured extinction spectrum (matrix M) and the computed extinction spectrum. The individual concentration elements of the concentration vector can be varied by trial and error to find the minimum least squares error, but the non-negative least squares algorithm based on a modified QR decomposition ensures that the solution does not get trapped in a local minimum. It is a deterministic approach that determines the global minimum solution. The matrix is computed assuming an arbitrary particle concentration (volume concentration), such as 1%. The actual concentration is then 1% times the concentration found by the non-negative least squares global minimum solution.

Figure 4:
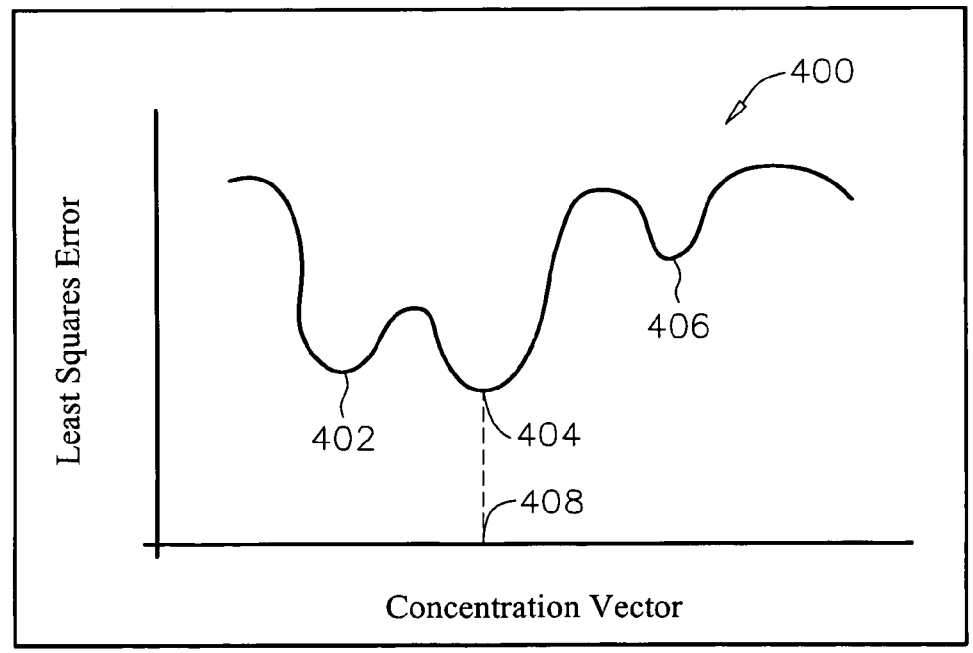
FIG. 4 illustrates a plot of the least squares error values against various concentration vectors c.

FIG. 4 illustrates a plot 400 of the least squares error values against the concentration vector c. As can be seen there are several local minima 402, 404, 406 in the plot. The present invention locates the global minimum 404 as the most probable solution for the measurement of the particle size distribution and concentrations of particles in the measured extinction spectrum represented by the measurement vector having been used with the reference matrix M to compute various concentration vectors c. Thus, in the example shown in FIG. 4, the most probable solution to the particle size distribution calculation is that given by the value of the concentration vector c plotted at 408. The calculated extinction spectrum obtained by multiplying this value of the concentration by the reference matrix M most closely matches the measured extinction spectrum.

The other local minima 402 and 406 might be identified as solutions in some prior art systems, due to the nature of different combinations of particle sizes sometimes producing measured extinction spectra that are very similar, as noted above. For example, a sample dilute colloid having 100 nm particles and 300 nm particles, when the measured extinction spectrum represented by the measurement vector is compared with the calculated spectrum obtained by multiplying the reference matrix M with various concentration vectors c, may provide alternative solutions, such as a solution at local minimum 402 indicating that the particles measured are all 200 nm particles, while the global minimum 404 indicates that the particles measured were 100 nm and 300 nm particles. By consistently finding the global minimum 404, the present system ensures that the most probable particle size distribution result is attained.

Artifacts

Figure 5A:
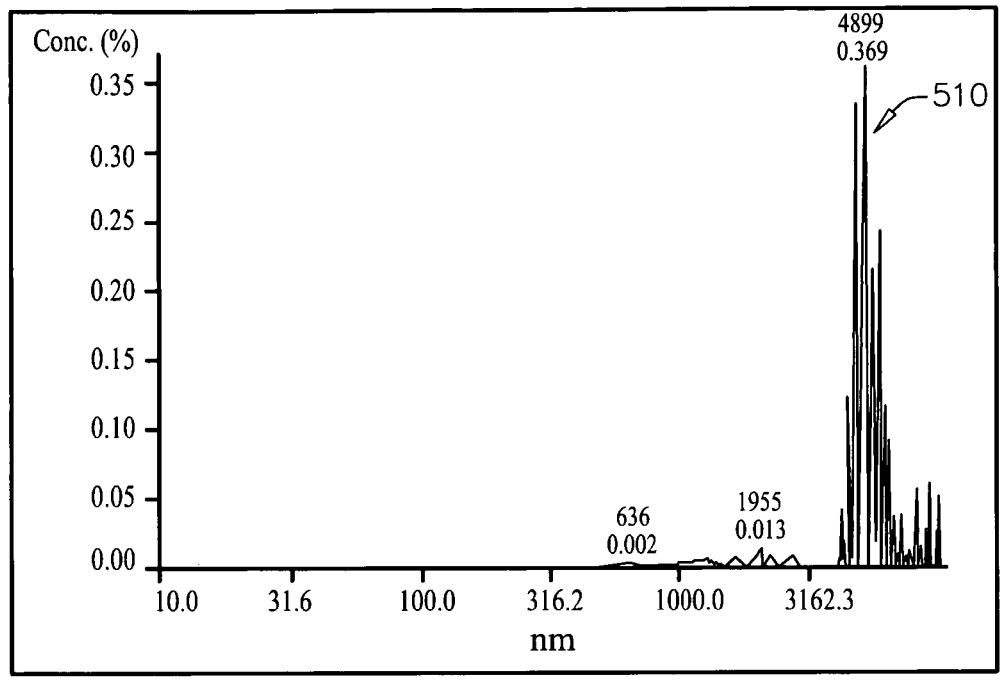
FIG. 5A shows a particle size distribution calculated from a measurement vector and reference matrix according to the present invention, when about 1% noise was present in the system.

The results of a particle size distribution calculated by the methods described above are typically quite spiky, especially when a significant amount of noise is present in the system. For example, FIG. 5A shows a particle size distribution 510 calculated from a measurement vector and reference matrix according to the techniques described above when about 1% noise was present in the system. The term "noise" here refers to the to the root mean square deviation of the noise waveform which is added to the signal, calculated as a percentage of the signal, as is commonly used in computing the signal-to-noise ratio, which is the inverse of the 1% noise referred to here. That is 1% noise means a 100 to 1 signal-to-noise ratio. In many usages, a 1% noise is not considered very significant and it can be difficult, as a practical matter to achieve lower noise levels. Because the 1% noise level does have a significant effect on the computed particle sizes, it is advantageous to post process these computed particle sizes.

Figure 5B:
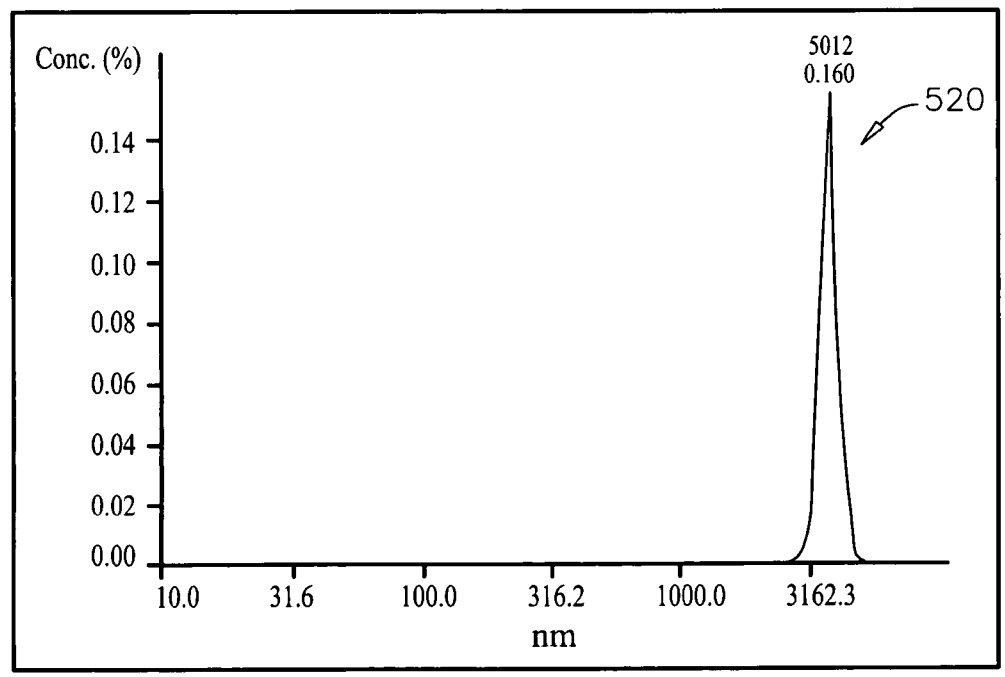
FIG. 5B shows the particle size distribution calculated from the same measurement vector and reference matrix used to calculate the particle size distribution of FIG. 5A, but where much less noise (substantially none) was present in the system.

FIG. 5B shows the particle size distribution 520 calculated from the same measurement vector and reference matrix used to calculate the particle size distribution 510, but where much less noise (substantially none) was present in the system. Because in practice, there is typically always some noise present, one or more smoothing techniques are applied to the calculated particle size distribution to smooth out the spikiness of the result. Spiky results are difficult for a user to interpret, since spiky results do not allow the user to simply locate a value along an axis of the plot by simply cross referencing it with a value along the other axis. At such location, there may be a discontinuity in the plot, or the value at such location may be substantially higher or lower than what it would be, if the spikiness were removed. Similar considerations apply to the interpretation of the particle size distribution or particle concentrations by a subsequent system. Further discussion of smoothing techniques that can be applied to reduce the spikiness of the particle size distribution result is provided below with reference to FIG. 10A.

Another noise artifact can occur when the particle size distributions of particles is broad. A broad particle size distribution is defined as a particle size distribution in which the number of non-zero particle sizes for which the particle concentration is greater than zero is greater than a predetermined percentage of the total number of particle sizes in the reference matrix M and therefore are present in the particle size distribution.

Inversion of the reference matrix resulting from a broad particle size distribution (PSD) spectra using the non-negative least squares (NNLS) algorithm can induce a noise artifact that causes the resulting particle size distribution to indicate an excess of large particles. That is, the computed particle size distribution will indicate the presence of large particles that are not really present in the sample. This artifact possibly arises because particles larger than the measurement wavelength do not contribute much detail to the extinction spectrum. A broad distribution of large particles simply looks like a nearly constant offset in absorption units over the wavelength range. When the particles are much larger than a wavelength, then they simply cast shadows on the detector. There is no spectral dependence. The spectrum is flat. Therefore no distinction can be made between one really large particle and two particles that each have half the cross-sectional area of the really large particle. Any spectrum that is flat can be fit by adding a distribution of large particles. The problem is that there is more than one solution to this "ill-posed" problem. Accordingly, the present techniques find the solutions with the minimum number of filled bins, which eliminates the broad distribution of large particles. Accordingly, when a broad distribution of particles is present, the present invention provides a method (a large particle artifact removal application) to eliminate this large particle noise. The large particle artifact removal application is described in detail below after a description of the example shown in FIG. 6.

A sample colloid including silicon nitride particles was prepared and its particle size distribution was measured according to the above-described methods. The silicon nitride was a NIST (National Institute of Standards) reference material 659, which is used for calibrating a sedigraph, an instrument that measures particle size by sedimentation. According to NIST, the particles should have the following cumulative weight distribution, as shown in Table 1 below.

TABLE 1

| Cumulative Weight Percentile | Certified Value (µm) | Uncertainty (µm) |
| --- | --- | --- |
| 10 | 0.48 | 0.10 |
| 25 | 0.81 | 0.10 |
| 50 | 1.43 | 0.10 |
| 75 | 2.08 | 0.11 |
| 90 | 2.80 | 0.13 |

Figure 6:
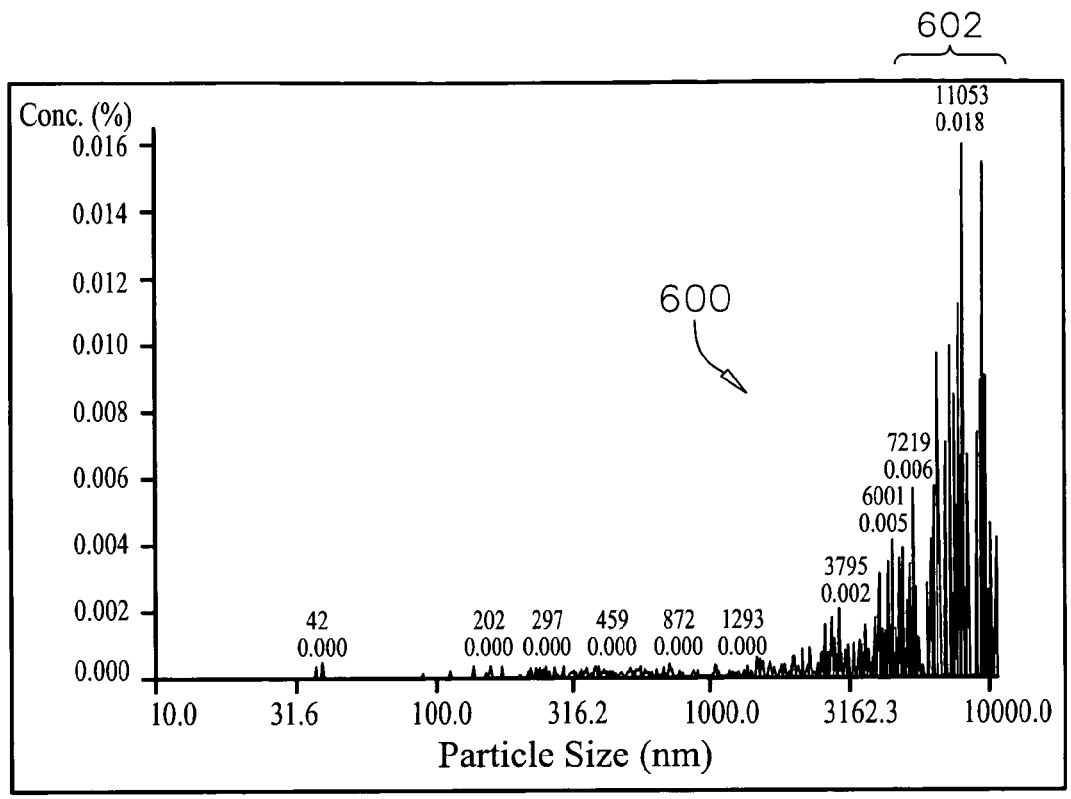
FIG. 6 is a particle size distribution plot illustrate large particle noise artifact.

The silicon nitride sample was prepared and then diluted to approximately 0.02165% by weight or 0.00679% by volume in water to provide the sample dilute colloid. The dilution was performed to enable sufficient light to be transmitted through the 1 cm path length cell 20 to make an extinction spectrum measurement with the 8453 spectrophotometer. A reference matrix M was computed using known data for the particle sizes, the refractive index of silicon nitride, and the refractive index of water. The resulting matrix M was a 911 row by 911 column matrix. The 911 columns covered a particle size range from 10 nm to 15 µm. The measurement vector representing the measured extinction spectrum of the sample colloid was input along with reference matrix M to a process that solves for the concentration vector c via the non-negative least squares method in a manner as described above. The PSD 600 that produced the best matching spectrum is shown in FIG. 6.

While the NIST data in Table 1 indicate that the sample has few particles greater than 3 µm in diameter, the raw particle size distribution 600 indicates that the bulk of the particles 602 constituting the sample are larger than 3 µm. Additionally, it can be observed that the total concentration of particles in the result 600 is too high at 0.0322% by volume rather than the prepared 0.00679%. However, the fit to the measured spectrum is quite good with an RMS fit error of 0.11%.

Figure 7:
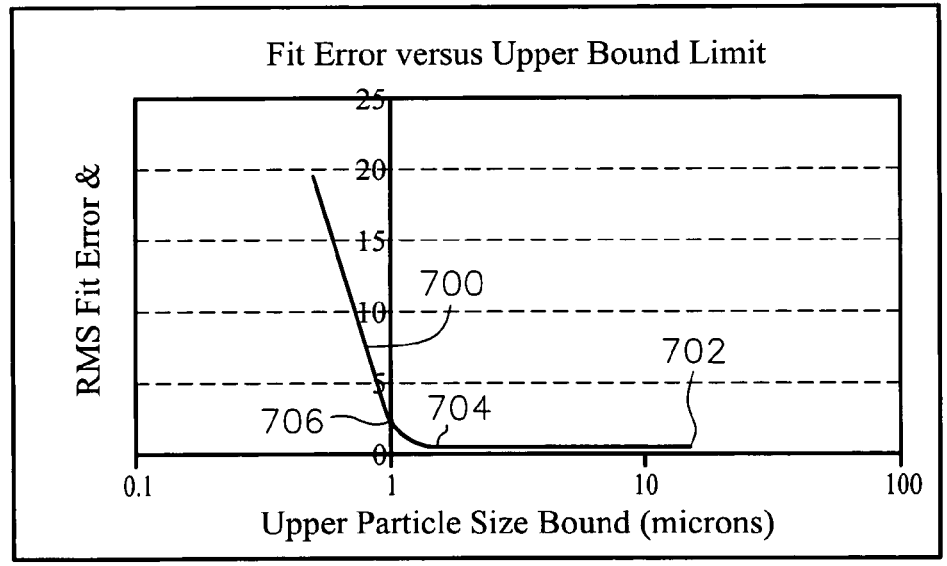
FIG. 7 illustrates changes in fit error relative to upper particle size bound limit.

The large particle artifact removal application provides a method of constraining the particle size range used in the inversion. In the example shown in FIG. 6, reducing the upper particle size range bound from 15 µm to about 3 µm had almost no effect on the fit error even though the particle size distribution changed significantly. These results are shown in FIG. 7. The RMS fit error 700 only slowly increases from about 0.11% when the particle size upper bound is set to 15 µm 702, to about 0.15% when the particle size upper bound is set to 1.5 µm 704. As the particle size upper bound is reduced below 1 µm 706, the fit error increases rapidly.

Figure 8:
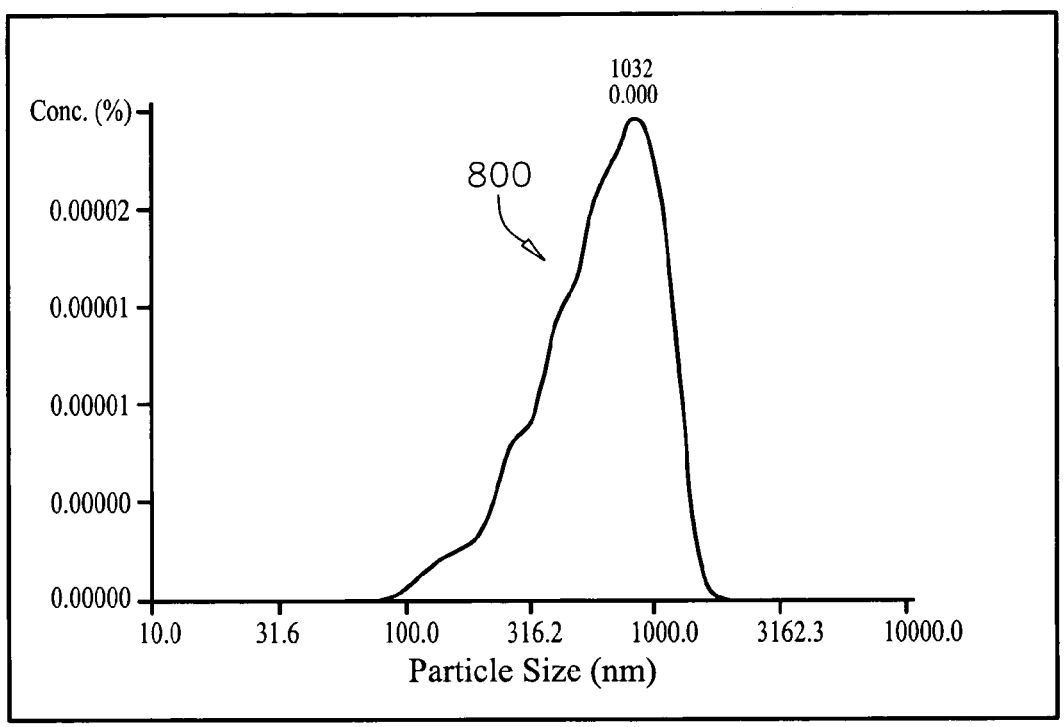
FIG. 8 shows the particle size distribution of FIG. 6, after post processing to remove large particle size artifact.

After constraining the maximum particle size to 1.5 µm, the resulting particle size distribution was smoothed, with a 3% factor to reduce the spiky particle size distribution result, the particle size distribution 800 shown in FIG. 8 was produced, and the total particle concentration result was calculated to be 0.0040% by volume. "Smoothing with a 3% factor" refers to the number of bins in the particle size distribution (the number of elements in the concentration vector). Smoothing is performed by convolving the particle size distribution with a Gaussian kernel with width equal to 3% of the total number of bins. Thus, if there are 100 bins, then the convolution kernel has a width of 3. This smoothing function is a Gaussian blurring function, similar to the Gaussian blur function provided in Adobe PHOTOSHOP, except it is a one dimensional blurring function, rather than the two-dimensional blurring function provided in PHOTOSHOP. An even better match to the known total particle concentration was calculated when the particle size upper bound was increased to 3 µm.

As shown, when the above-described calculation methods result in broad particle size distributions, the raw particle size distribution results should be post-processed to eliminate large particle noise. The large particle artifact removal application provides one solution to reducing or removing large particle noise. Other post-processing techniques may be alternatively applied. For example, the particle size distribution results can be fit to a log-normal distribution to reduce or eliminate large particle noise.

Another artifact to address is one that can occur in the extinction spectra measured by the spectrophotometer, and is referred to as forward scattering artifact. The above-described scattering attenuation model assumes that all light that is scattered is lost. For the most part this is true. However a small portion of the light that is scattered in the forward direction is captured by the receiving optics 24. The amount of forward scattering depends on the ratio of the particle size to the illuminating wavelength as well as the capture angle of the receiving optics.

Figure 9A:
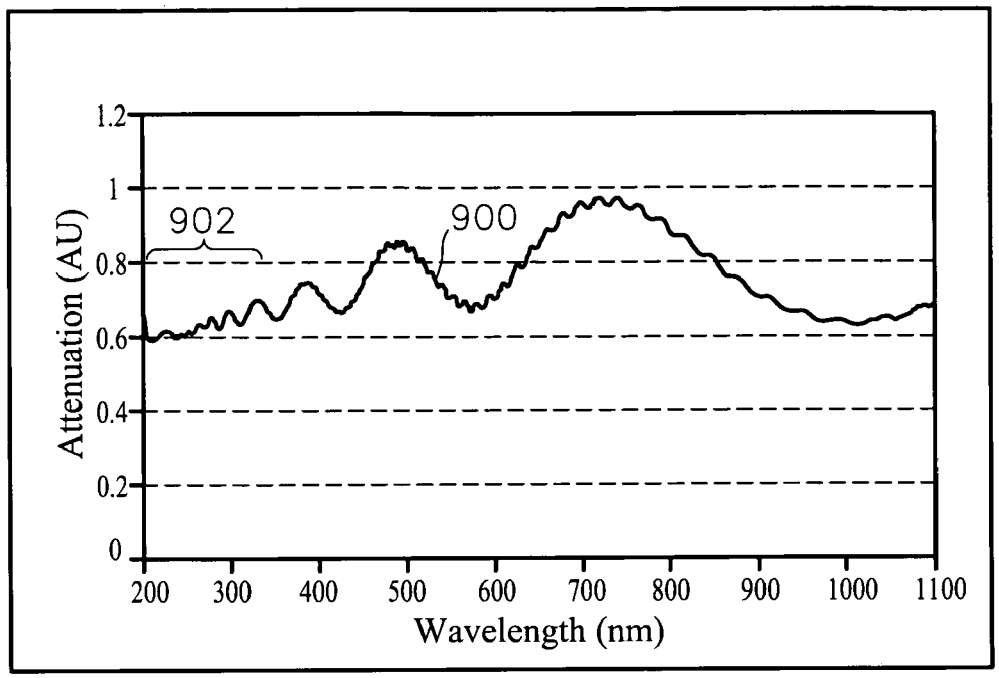
FIG. 9A illustrates forward scattering artifact in an attenuation plot.
Figure 9B:
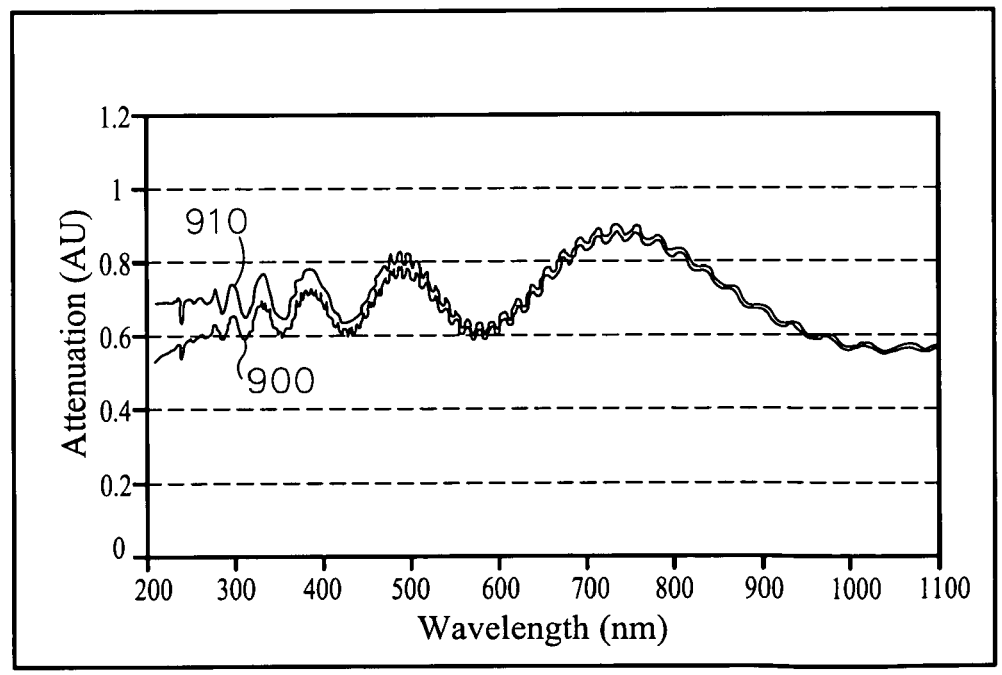
FIG. 9B illustrates a plot having been corrected for forward scattering artifact by applying a forward scattering correction factor.

When the extinction spectrum for large particles is measured, the forward scattering artifact reduces the total attenuation observed, particularly at short wavelengths, where the size-to-wavelength ratio becomes large. An example of this reduction is shown in the extinction spectrum plot 900 in FIG. 9A, where the attenuation in the portion 902 of the plot 900 of the measured extinction spectrum of 5 µm polystyrene particles has been reduced due to forward scattering. FIG. 9B illustrates a plot 910 corrected for forward scattering artifact by applying a forward scattering correction factor to plot 900. Plot 900 is also shown for comparison.

A method for calculating attenuation in absorbance units per unit length (AU/L) as a function of the relative extinction cross-section $Q_{ext}$ was described above. A method for calculating the forward scattering correction factor, represented by $\Delta AU/L$ is now described. This forward scattering correction factor is subtracted from the raw absorbance per unit length to give the forward-scattering-free AU/L to get a more accurate scattering model. Assuming that the spectrophotometer admits a cone of scattered light with half angle β, then it can be shown that the correction factor in AU per unit length L is $$\frac{\Delta AU}{L} = \frac{3\log e}{16\pi^3} \frac{C_v}{a^3} \frac{\lambda^2}{n_f^2} 2\pi \int_0^\beta |X(\theta)|^2 \sin(\theta) d\theta, \quad (7)$$

where $|X(\theta)|^2$ is the magnitude squared of the vector scattering amplitude as defined in Bohren and Huffman.

For small particles and small limiting angles β, then equation 7 reduces to the approximate expression:

$$\frac{\Delta AU}{L} \cong \frac{3\log e}{16\pi^3} \frac{C_v}{a^3} \frac{|S_1(0°)|^2 \lambda^2}{n_f^2} \Delta \Omega, \quad (8)$$

where it is assumed that $|X(\theta)|^2 \cong |X(0°)|^2 = |S_1(0°)|^2$ for all $\theta \leq \beta$ the instrument acceptance angle. In addition the solid angle $\Delta\Omega$ of the conical beam of half angle β is given by $$\Delta\Omega = 2\pi(1-\cos(\beta)) \quad (9)$$

If β is 0.8 degrees, then $\Delta\Omega=0.000612$ sterradians. The solid angle $\Delta\Omega$ is a fixed property of the spectrophotometer.

Post Processing

Figure 10A:
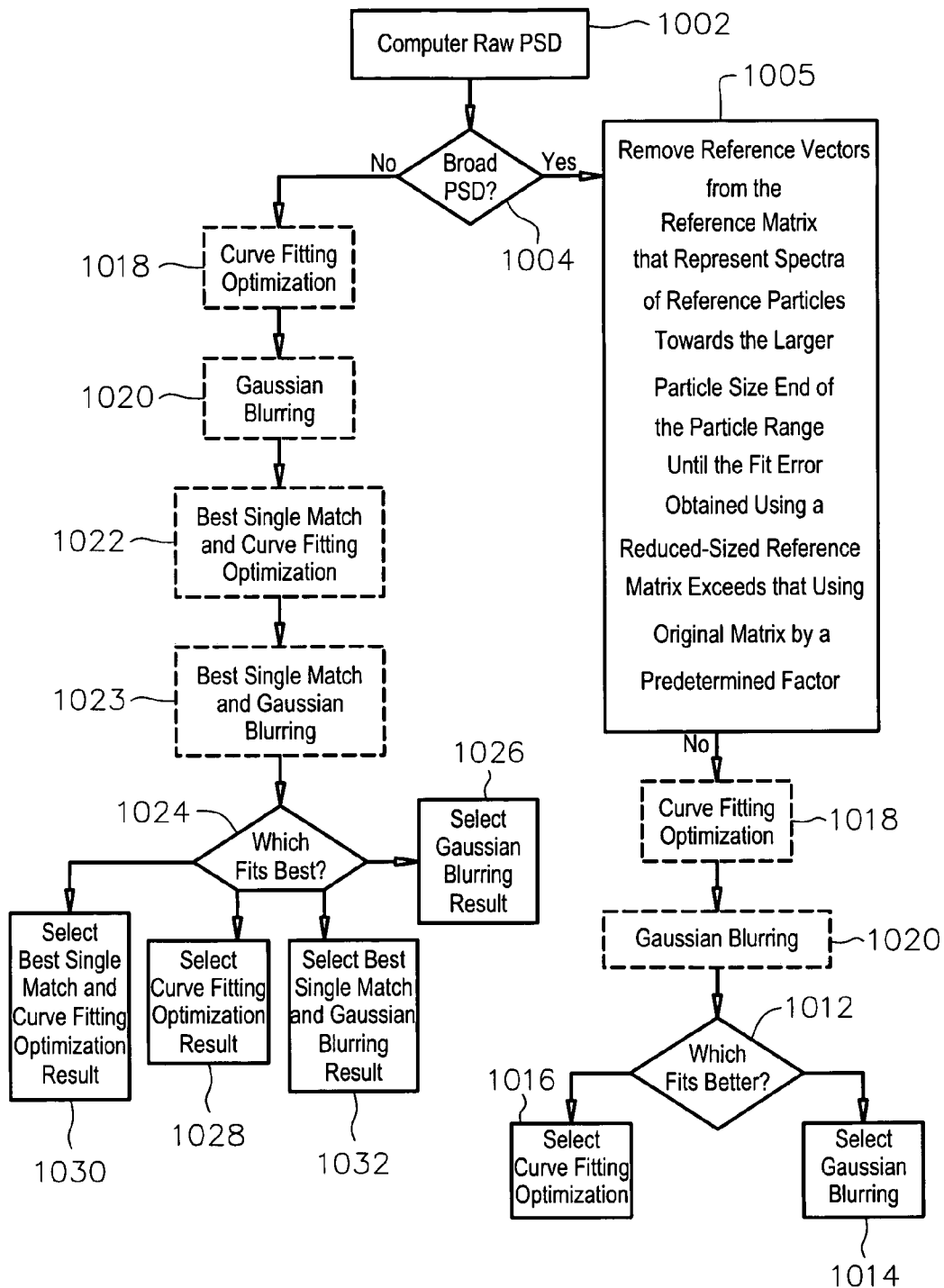
FIG. 10A is a flow diagram illustrating post processing methods that can be performed after computing a particle size distribution of a sample dilute colloid according to the present invention.

FIG. 10A is a flow diagram illustrating post processing methods that can be performed after computing a raw particle size distribution of a sample of small particles. These methods can be implemented for automatic processing by the system, such as by one or more computer processors incorporated into the system, to produce the most probable particle size distribution and particle concentration results for a sample that constitutes part of a sample dilute colloid whose extinction spectrum has been measured by spectrophotometry. At 1002, the raw particle size distribution (PSD) is calculated according to methods described above. For example the NNLS algorithm may be applied to the measurement vector and a reference matrix M to calculate the particle size distribution and particle concentrations of the particles. At 1004 it is determined whether the raw PSD is a broad particle size distribution. A broad particle size distribution is defined as a raw particle size distribution in which the number of particle sizes for which the particle concentration is greater than a threshold particle concentration, in greater than a predetermined percentage of the total number of particle sizes in the reference matrix M. In one example, a broad particle size distribution is defined as a raw PSD having a particle concentration greater than a threshold particle concentration of zero in greater than 3% of the total number of particle sizes.

When it is determined at 1004 that the PSD is a broad PSD, then post processing to eliminate large particle noise is carried out. For example, the large particle artifact removal application is applied at 1005 to remove reference vectors from the reference matrix that represent spectra of reference particles towards the larger particle size end of the particle range, until the fit error obtained using a reduced-size reference matrix exceeds that using the original reference matrix M by a predetermined factor.

Figure 10B:
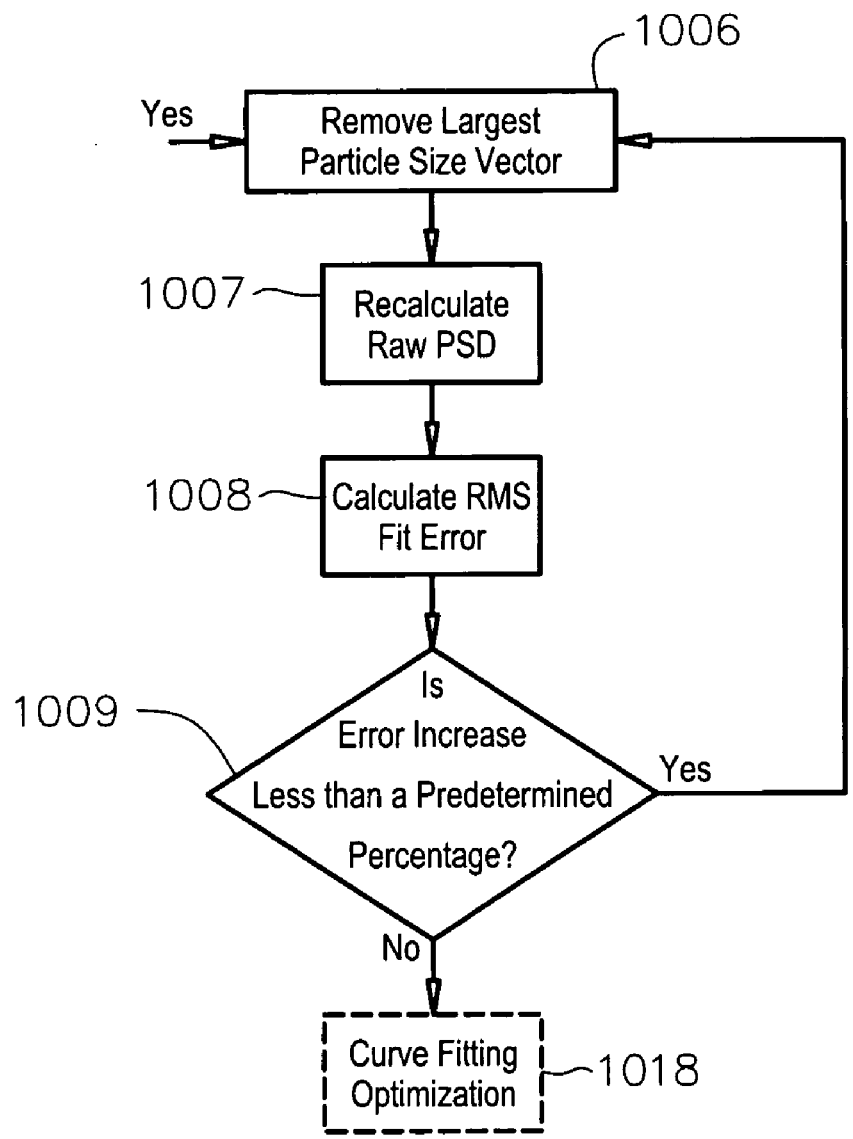
FIG. 10B is an embodiment of a subroutine that can be practiced in the process of FIG. 10A
Figure 10C:
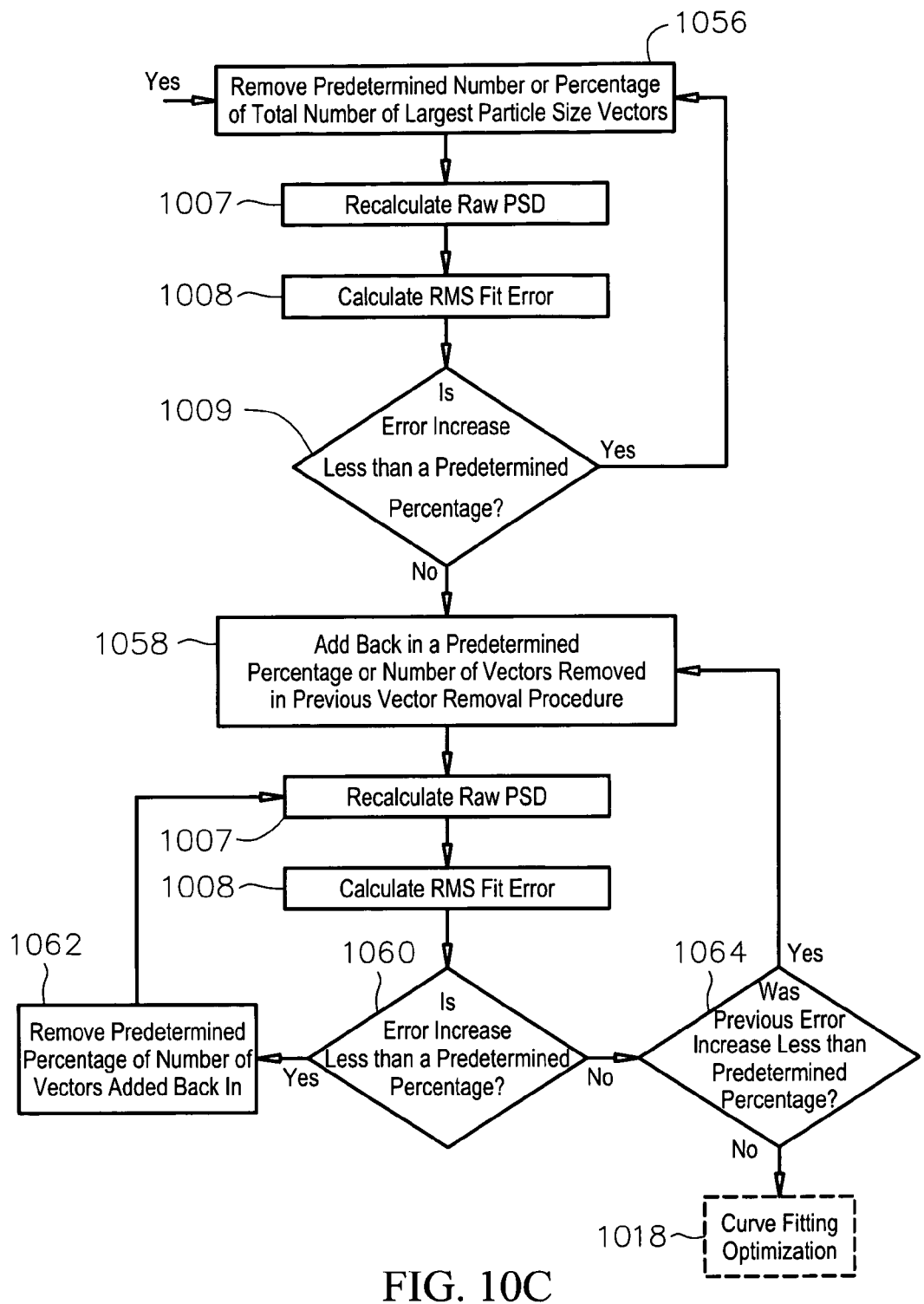
FIG. 10C is an alternative embodiment of a subroutine that can be practiced alternatively to that of FIG. 10B.

The process of removing reference vectors from the reference matrix can be performed according to various different schemes. FIG. 10B illustrates a subroutine 1006-1009 as one example of carrying out the process described in 1005 in FIG. 10A, to iteratively remove the largest particle size vector. At 1006, the column representing the largest size particle is removed from reference matrix M to generate a new, smaller reference matrix. At 1007, the raw PSD is recalculated, using the new, smaller reference matrix resulting from eliminating from reference matrix M the column vector representing the largest particle size. The RMS error in the fit between the measured spectrum and the spectrum calculated using the reduced-size reference matrix and the recalculated raw PSD of the current iteration is calculated at 1008. The current RMS fit error is compared with the original RMS fit error calculated in a manner described above, between the measured extinction spectrum and the calculated extinction spectrum calculated using the original, full-size reference matrix M and the raw PSD calculated at 1002. If the error increase percentage calculated by the difference between the current RMS Fit Error and the original RMS fit error calculated using the full-size reference matrix, divided by the original RMS fit error, is less than a predetermined percentage, then processing returns to 1006 to perform another iteration of 1006, 1007, 1008 and 1009, beginning with removing the largest remaining particle size vector at 1006 to again reduce the reference matrix M. Once the RMS error difference between the current RMS error and the original RMS error is greater than or equal to a predetermined percentage (in one non-limiting example, twenty percent), then the iterative process is ended ("No" at 1009) and the upper particle size bound has been determined, as well as the smallest practical reference matrix M to use in calculating the PSD.

As noted, this process is not limited to removing one bin at a time, as more than one bin at a time may be removed to make the process faster. FIG. 1C illustrates an alternative, preferred process for large particle artifact removal, wherein 1056, 1007-1009, 1058, 1007-1008, 1060, 1062, 1064 and 1018 are substituted for 1005 and 1018 of FIG. 10A in order to post process a broad PSD. Thus, when it is determined at 1004 that a broad PSD exists, a predetermined number or percentage of the total number of bins are removed at 1056, where the bins removed are the largest particle size bins. At 1007, the raw PSD is recalculated, using the new reduced-size reference matrix resulting from eliminating the columns representative of the largest particle size bins removed at 1056. The RMS error in the fit between the measured spectrum and the spectrum calculated using the reduced-size reference matrix and the calculated raw PSD of the current iteration is calculated at 1008. The current RMS fit error is compared with the RMS fit error of the RMS fit error having been calculated, in a manner described above, using the measured spectrum, the spectrum calculated using the original, full-size reference matrix and the raw PSD calculated at 1002. If the error increase percentage calculated by the difference between the current RMS fit error and the original RMS fit error calculated using the full-size reference matrix, divided by the original RMS fit error, is less than a predetermined percentage, then processing returns to 1056 to perform another iteration of 1056, 1007, 1008 and 1009, beginning with again removing the predetermined number or percentage of the total number of bins remaining constituting the largest remaining particle size bins at 1056 to again reduce the reference matrix M.

If the error increase percentage at 1009 is not less than the predetermined percentage, then at 1058 a predetermined percentage (rounded to nearest integer) of the number of bins removed in the previous removal procedure are added back in to increase the size of the matrix M. The bins added back in are the smallest ones from the total number of bins in the previous removal. The raw PSD is again recalculated (1007) and the RMS Fit Error is again calculated (1008) using the latest revise matrix M. If at 1060, the error increase is less than a predetermined percentage, when comparing the current RMS fit error to the RMS fit error and the original RMS fit error in a manner described above, then a predetermined percentage (rounded to the nearest integer) of the number of bins that were added back in at 1058 are removed at 1062. The bins that are removed are the largest ones from the group of bins previously added back in. The 1007, 1008 and 1060 are again executed, and this loop is iterated until a "No" answer is reached at 1060. When the error increase is not less than the predetermined percentage at 1060, then it is determined whether the iteration of 1060 just prior to the current one found an error increase less than the predetermined percentage. If Yes, then another iteration of 1058, 1007, 1008 and 1060 are performed. If No, than processing proceeds to 1018 as indicated in FIG. 10B as well as FIG. 10A.

In one embodiment, the predetermined percentage is 50%. Thus, for example, if there are originally 400 bins, then 200 bins are removed at 1056, 100 bins are added back in at 1058, and 50 bins are removed at 1062, etc.

When the PSD is determined not to be a broad PSD at 1004, then post processing for large particle size noise is not needed, and the particle size distribution data is smoothed using at least one of four methods 1018, 1020, 1022 and 1023. Method 1018, referred to as "curve fitting optimization" fits multiple Gaussian curves to the PSD to smooth the PSD. The "Gaussian blurring" method at 1020 is another technique that can be used to smooth the PSD. The best single match technique forces the solution to find a single size bin of the reference matrix M that gives the best fit, as an alternative to computing the PSD by non-negative least squares calculations or any other least square algorithm or other algorithm described above for inverting the reference matrix M. The best single match approach forces all the bins but one to zero. Since a single-bin solution is not very likely, this solution is smoothed by one of two methods. The first smoothing technique fits a Gaussian with three fitting parameters: the mean, the standard deviation, and the concentration. The best RMS fit is achieved by starting with the best single match solution as the mean, but allowing both the mean and the standard deviation to wander. The simple smoothing algorithm effectively broadens the single bin by a fixed standard deviation (the 3% factor mentioned above determines the width). Alternatively a log-normal distribution can be used instead of a Gaussian. Method 1022 uses the best single match technique and then smoothes by the "curve fitting optimization" method 1018. Method 1023 uses the best single match technique and then smoothes by Gaussian blurring 1020.

At 1024, when more than one of the above-described smoothing processes 1018, 1020, 122 and 1023 is performed, the best fitting one of the results provided by the smoothing processes performed is identified. If only one of the smoothing processes is performed, the solution produced by that process is used. Assuming more than one of the smoothing processes is performed, the best fit is determined at 1024 by comparing the RMS fit error for each of the methods and choosing the smallest. The result of the best fitting method is then selected and applied at 1026, 1028, 1030 or 1032, depending upon which method is determined to provide the best fit, thereby providing the smooth particle size distribution and particle concentrations results. Optionally, the best fit solution can then be displayed, such as on a user interface, or otherwise output for use by a human user. Further optionally, in addition or alternative to displaying, the best fit solution can be passed to subsequent processing for use, e.g., in controlling a process that generates the particles subject to analysis.

After performing large particle noise suppression as described above, curve fitting optimization may be performed at 1018, and/or Gaussian blurring may be performed at 1020 on the PSD calculated using the reduced-size reference matrix resulting in the last iteration of 1006, 1007, 1008 and 1009. At 1012, the better fitting result from the processes 1008 and 1010 is identified, when more than one of these processes is performed. If only one is performed that it is the solution that is used. Assuming more than one is performed, the better fit is determined by comparing the RMS fit error for each of the methods and choosing the method resulting in the smaller RMS fit error. The result of the better fitting method is then selected and applied at 1014 or 1016, depending upon which method is determined to provide the better fit, thereby providing the smooth particle size distribution and particle concentrations results. Optionally, the better fit solution can then be displayed, such as on a user interface, or otherwise output for use by a human user. Further optionally, in addition or alternative to displaying, the better fit solution can be passed to subsequent processing for use, e.g., in controlling a process that generates the particles subject to analysis.

Computing Particle Refractive Indices

Refractive index data for the wavelength range over which the spectra used by the particle size distribution measurement processes described above are measured or calculated are often very difficult to obtain. In such cases, the processes described above can be used to determine refractive index data from a measured extinction spectrum measured for a sample colloid in which the particle size distribution is known and particle concentrations are known. Once obtained, this refractive index data can then be used to compute the particle size distribution and particle concentration for a sample of particles of the same particle material and whose particle size distribution is unknown, but the particle sizes are within the range of particle sizes of the process described herein.

As described above, particle size distributions and particle concentrations can be calculated for a sample of small particles when the refractive indices at respective wavelengths within the measurement wavelength range of the particle material and the fluid of a sample colloid are known and the measured extinction spectrum of the sample colloid is provided. Conversely, if the measured extinction spectrum and the particle size distribution in the sample colloid are known, the refractive index/indices over the measurement wavelength range of the particle material(s) can be calculated to provide a refractive index vector. However, this is also a difficult problem to solve, mainly because there are multiple solutions for the refractive index (RI) vector all but one of which are wrong. Below are three embodiments of methods for calculating refractive index according to the present invention.

Generally, when computing a refractive index vector (representing wavelength, real refractive index, and imaginary refractive index) of the particle material of a sample of small particles, a sample colloid is provided in which the particle size distribution of the small particles in the sample colloid is known. The sample colloid is a dilute colloid. The real refractive index value is an indicator of how much light is scattered and the imaginary refractive index value is an indicator of how much light is absorbed and turned into heat. A measured extinction spectrum of the sample colloid is obtained, based on spectrophotometric measurement of the small particles in the sample colloid at discrete wavelengths. An objective function of refractive index values is minimized as a function of wavelength. This is done in substantially the same way as solving for the concentration vector, but where the refractive index is found that minimizes the error between the measured extinction spectrum and that computed from the known particle size distribution, using the same Nelder-Meade algorithm to determine the refractive index vector of the particle material of the small particles.

Since it is often difficult to obtain a monodisperse sample of small particles for refractive index measurement, the present methods and system include the capability to enter a measured particle size distribution along with the measured extinction spectrum. When the refractive index of the particle material is to be measured, the particle size distribution is measured using a method that does not require the refractive index of the particle material to be known. Typically the particle size distribution measurements are provided in the form of histograms on a spread sheet or other flat file. However, a PSD can be provided in other formats, as all a computer needs is a table of particle size and numerical concentration for each possible particle size. Accordingly, the algorithms are programmed to read a text or .csv file containing the data representing the particle size distribution as a set of (particle size, concentration number) vectors. After the data are read, the particle concentrations are converted from a number density (number of particles pre unit volume of colloid) to a particle volume fraction. Particle volume fraction is related to particle number density by the following equation:

$$C_v = \frac{4}{3}\pi a^3 N \quad (12)$$

where N is the number density, a is the particle radius, and $C_v$ is the calculated volume fraction. In this case, a is known. The total number of particles measured in the sample is not the number density, but is assumed to be proportional to the number density N. However, the particle size distribution information can be used to generate a normalized PSD by volume. Equation (12) is used to calculate a volume fraction for each particle size. That is, for each particle size, the volume fraction for that particle size is calculated by multiplying the number density of particles of that particle size by the cube of the particle radius of the particles of that particle size, and a constant, as noted above in equation (12). The calculated volume fractions, plotted against the particles sizes, gives a distribution proportional to particle volume. The distribution is then normalized so that the sum of the particle volume fractions is 1.

The normalized PSD together with the total volume fraction of particles can then be used to calculate refractive index. Calculation of the extinction spectrum of a sample dilute colloid having a monodisperse particle size distribution has already been described above, including calculating AU(λ) as a function of wavelength including the forward scattering component. For sample dilute colloids with a polydisperse particle size distribution, linear methods of solving are also applied, as a summation over the particle size distribution is performed to compute the spectrum. That is, the extinction as a function of wavelength is computed as follows:

$$AU(\lambda, n_p, n_f) = C_v \sum_n PSD(a_n) AU(\lambda, a_n, n_p, n_f) \quad (13)$$

where CV is the total volume concentration, $PSD(a_n)$ is the normalized volume fraction at the nth particle size an in the particle size distribution (as described in the previous section), and A U(λ, $a_n$, $n_p$, $n_f$) is the computed absorbance with unity volume concentration at wavelength λ and particle size $a_n$. $n_p$ and $n_f$ are refractive indices of the particle material and the fluid, respectively. Equation (13) is used extensively in all of the refractive index fitting algorithms described below.

The objective or cost function that the algorithms minimize is:

$$|AU(\lambda,n_p,n_f)-V_m(\lambda)|^2 \quad (14)$$

where $V_m$ is the measured extinction spectrum. That is, the algorithms function to find $n_p$ as a function of wavelength that minimizes equation (14). In the first and third methods/algorithms described below, this minimization is performed at each wavelength in the measured extinction spectrum, typically 92 wavelengths spaced by 10 nm. In the second method/algorithm described below (Sellmeier fit), the objective function (14)) is calculated for each wavelength in the wavelength range of the measured extinction spectrum and summed over all the wavelengths to give a measure of the overall fit quality.

One method of calculating refractive indices will be referred to as a point-by-point refractive index solver. Using this method, the measured extinction spectrum of the sample colloid, the PSD of the sample colloid, the concentrations of the particles of each of the particle sizes in the sample colloid, the transparent wavelength range (the spectral region in which there is no significant absorption, that is, the imaginary refractive index is essentially zero, and therefore only the real refractive index is solved for), and an initial refractive index. Since the extinction coefficient measured by the spectrophotometer depends on both the refractive index and the particle concentration, the method requires an input of the concentration vector to calculate the refractive index. Alternatively, if the refractive index at one wavelength is known, this can be used to calculate the concentration. This technique can therefore be used when the concentration is not known or when a refractive index for the particle material at a particular wavelength is known. Often the refractive index at the sodium d-line (589 nm) can be found in the literature. The program then computes the real refractive index at successive user-specified wavelength intervals starting at the longest wavelength and finishing at the absorption edge specified by the shortest wavelength in the transparency range. A refractive index maximum slope limit prevents the algorithm from jumping discontinuously to an incorrect solution. The method works well for smaller particles, e.g., particle sizes less than about 0.6 μm. For larger particles, the slope constraint is not sufficient to avoid wrong solutions.

To use the point-by-point refractive index solver, a user inputs (or, alternatively an automatic input can be performed of) the measured extinction spectrum of the sample colloid, the cell length, the PSD (including the particle concentrations), the transparent wavelength range (which may be user specified), the wavelength interval between RI calculations, and a starting RI at the longest wavelength in the transparent wavelength range. The user also enters (or the system may automatically enter, upon receiving these as inputs) slope constraints that take the form of an allowed incremental change in the refractive index n for a wavelength step. The transparent wavelength range may not always be known, but it can be discovered indirectly by checking to see if the RI fits to different PSDs of the same particle material give the same result. After solving for the refractive index as a function of wavelength, a plot of the objective function (equation 14) can be made against wavelength to easily identify where the real refractive index solution begins to fail. It is sometimes possible to detect the onset of absorption by looking at features in the extinction spectrum.

Figure 11A:
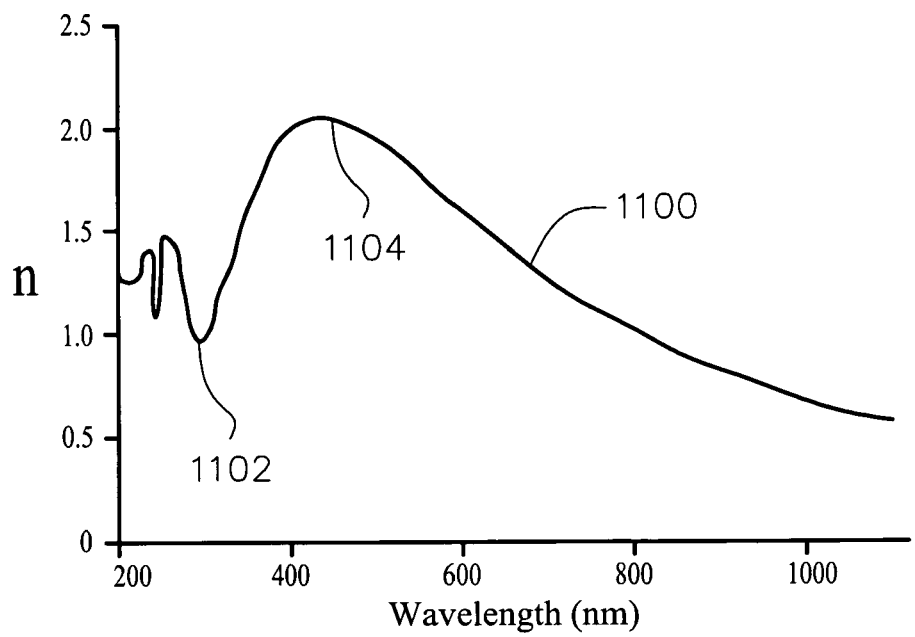
FIG. 11A is a plot of the scattering spectrum (attenuation spectrum) from 1 μm polystyrene particles prepared by Dow Chemical at a concentration of about 0.1% by volume in water.
Figure 11B:
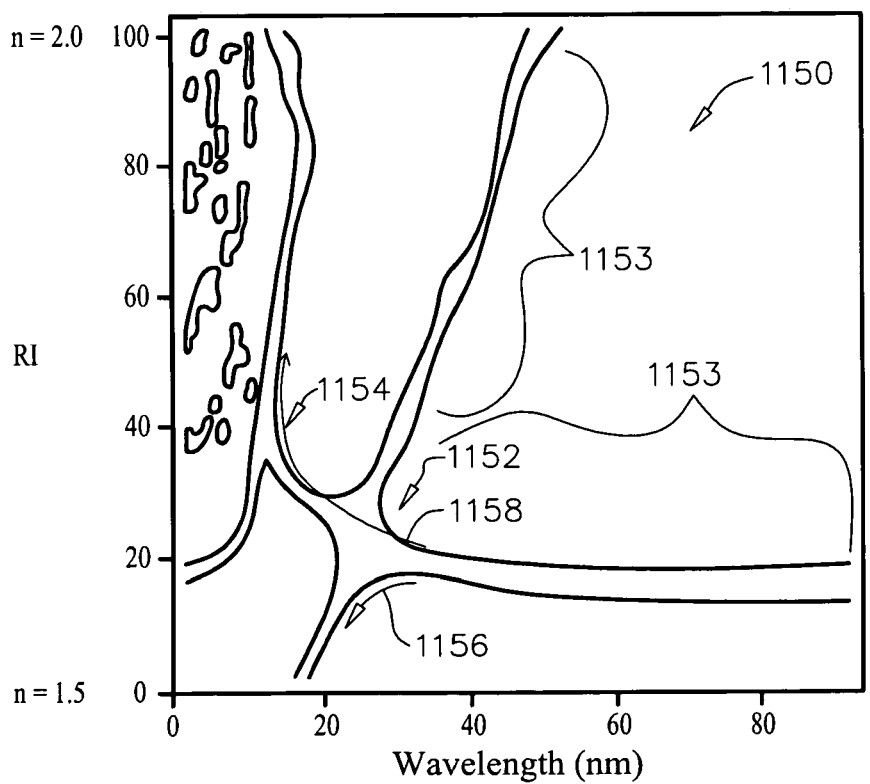
FIG. 11B is a plot of an objective function (equation (14)) as a function of wavelength and real particle refractive index.
Figure 11C:
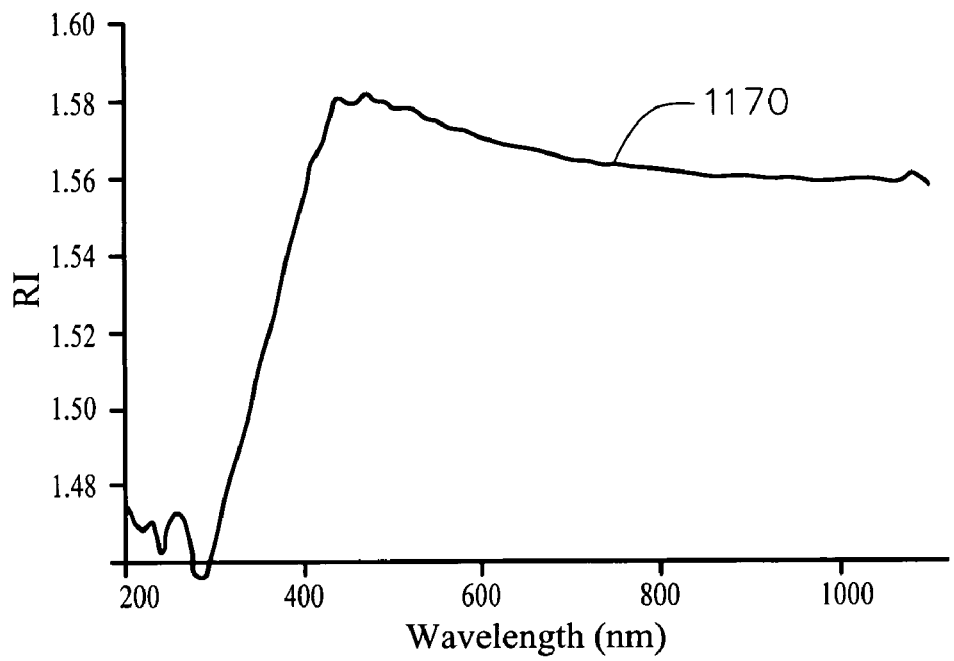
FIG. 11C illustrates a plot of refractive index results versus wavelength, as calculated using a point-by-point real refractive index solver application.

As noted previously, the point-by-point refractive index solver may have difficulty finding the correct solution for a calculation of RI of larger size particles. FIG. 11A is a plot 1100 of the measured extinction spectrum of a sample colloid in which 1 μm polystyrene particles prepared by Dow Chemical are dispersed at a concentration of about 0.1% by volume in water. When the objective function (equation (14)) is plotted as a function of wavelength and real particle refractive index, the two-dimensional "roadmap" of potential refractive index solutions 1150 is plotted, as shown in FIG. 11B. The shaded regions 1153 correspond to an objective function magnitude $<10^{-4}$, where the fit is good. Note that there are multiple solutions in regions where the wavelength becomes much shorter than the particle size. The cross-over regions 1152, 1154 correspond to inflection point regions 1102, 1104 on the spectrum curve 1100 of FIG. 11A. The problem with the point-by-point method is that it tends to take the lower path as indicated by arrow 1156 in the objective function plot, whereas, in this case, the correct solution is arrived at by taking the upper path indicated by arrow 1158. FIG. 11C illustrates the result 1170 found by the point-by-point method for this example, taking the pathway of arrow 1156, with an allowed incremental RI change of +/−0.05 in a 10 nm wavelength increment.

Figure 11D:
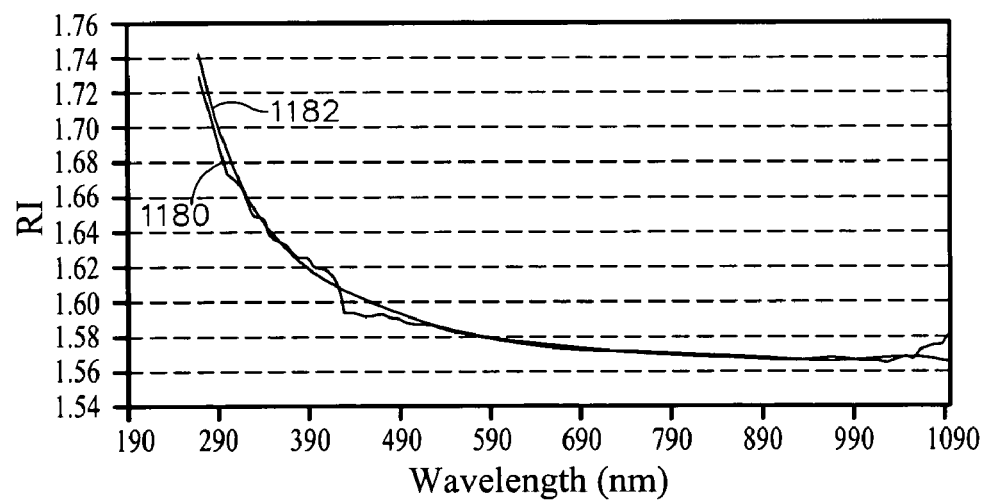
FIG. 11D shows plots of refractive index results versus wavelength, as calculated using a point-by-point real refractive index solver application, for 1 μm polystyrene particles and for 300 nm polystyrene particles.

Tightening the allowed incremental RI change (slope tolerance) to +0.02/−0.0001 RI in a 10 nm wavelength increment caused the point-by-point method to stay on the right path 1158, but the resulting RI curve 1180 was still too jagged especially near the inflection points, as illustrated in FIG. 11D. For comparison purposes, to illustrate the jaggedness of the RI curve 1180 for 1 μm polystyrene particles, the RI curve 1182 for 300 nm polystyrene particles that was calculated by the point-by-point method under the same conditions is shown. Only results for wavelengths longer than 270 nm have been plotted. It can be readily observed that curve 1182 is much smoother. The curve 1182 was found to work well for polystyrene samples, and was a better RI estimate than the RI estimate provided by curve 1180 for the 1 μm polystyrene particles.

Four different constrained optimization routines were used as alternatives for finding the refractive index vector as a function of wavelength that minimizes the objective function (equation (14)) in the constrained RI range. These were Nelder-Mead, Differential Evolution, Simulated Annealing, and Random Search, all of which are built into MATHEMATICAL®. The Nelder-Mead routine, also known as the simplex method, was preferred because it is substantially faster than the others. The second preferred routine was the Differential Evolution routine, which is described by the MATHEMATICAL® user guide as computationally expensive, but relatively robust and tends to work well for problems that have more local minima.

A second method of calculating refractive indices is referred to as the Sellmeier real refractive index solver. Using this method, the real refractive index is fit to a smooth curve. Unlike the point-by-point method, the Sellmeier equation is based on a physical model for dispersion. It ensures that the solution is continuous and has normal dispersion (the refractive index decreases with increasing wavelength). It also suppresses measurement noise. This prevents the jagged errors that can occur when calculating refractive indices using larger-size particles, and the point-by-point approach are avoided. The smooth curve that the real refractive index is fitted to is derived from the Sellmeier equation, which is often used to describe the refractive index dispersion of optical materials. The Schott Glass catalog (Schott AG, Mainz, Germany) lists the six Sellmeier coefficients for an extensive set of optical glasses and states that the refractive index is accurate to 5 parts per million. Excellent results were achieved by fitting a spectrum, calculated using the polystyrene RI determined using the Sellmeier equation to the measured extinction spectrum.

The Sellmeier equation is an empirical relationship between refractive index and wavelength that is commonly used to describe dispersion of optical glasses. The usual form for glasses is:

$$n^2(\lambda) = 1 + \frac{B_1 \lambda^2}{\lambda^2 - C_1} + \frac{B_2 \lambda^2}{\lambda^2 - C_2} + \frac{B_3 \lambda^2}{\lambda^2 - C_3} \qquad (15)$$

Figure 12A:
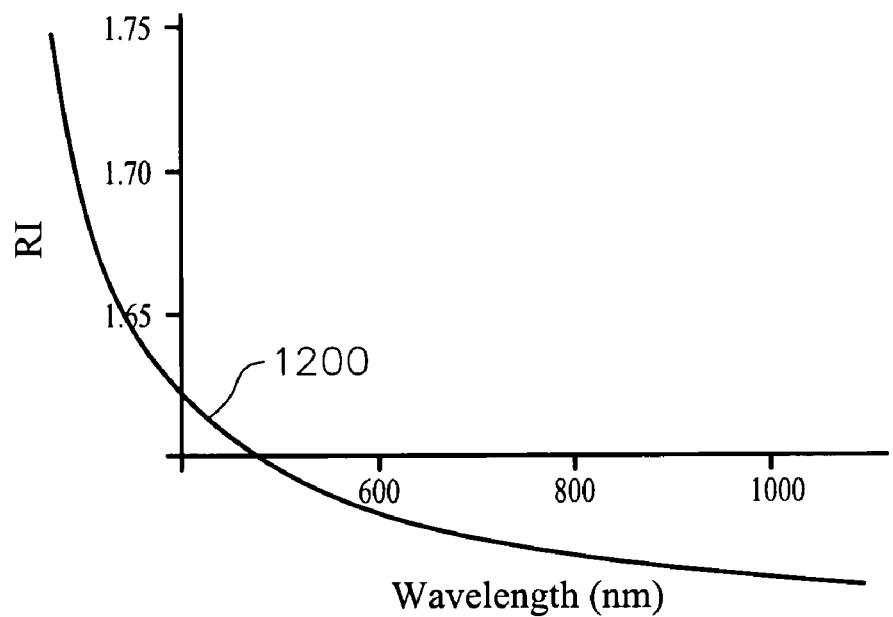
FIG. 12A shows a plot of refractive index results versus wavelength, as calculated using a Sellmeier real refractive index solver application, for 3 µm polystyrene particles.

The optimization strategy for the Sellmeier fit involves finding the six Sellmeier coefficients that produce the best fit over the entire spectrum. Thus the objective function for use with the Sellmeier real refractive index solver is defined as:

$$\sum_i |AU(\lambda_i, n_p, n_f) - V_m(\lambda_i)|^2 \qquad (16)$$

where summation is performed over all of the wavelengths in the measured extinction spectrum $V_m$. The Schott Glass catalog was referenced to select the minimization constraints for the Sellmeier coefficients. These constraints can be as follows, but are subject to change as this method is further refined: 0.4<B1<1.5, 0.1<B2<0.8, 0.7<B3<2.0, 0.001<C1<0.03, 0.005<C2<0.035, 80<C3<130. Using the same Nelder-Mead minimization algorithm used for the point-by-point refractive index solver described above, the refractive index result 1200 for 3 μm polystyrene particles was produced as shown in FIG. 12A, using the Sellmeier real refractive index solver.

Figure 12B:
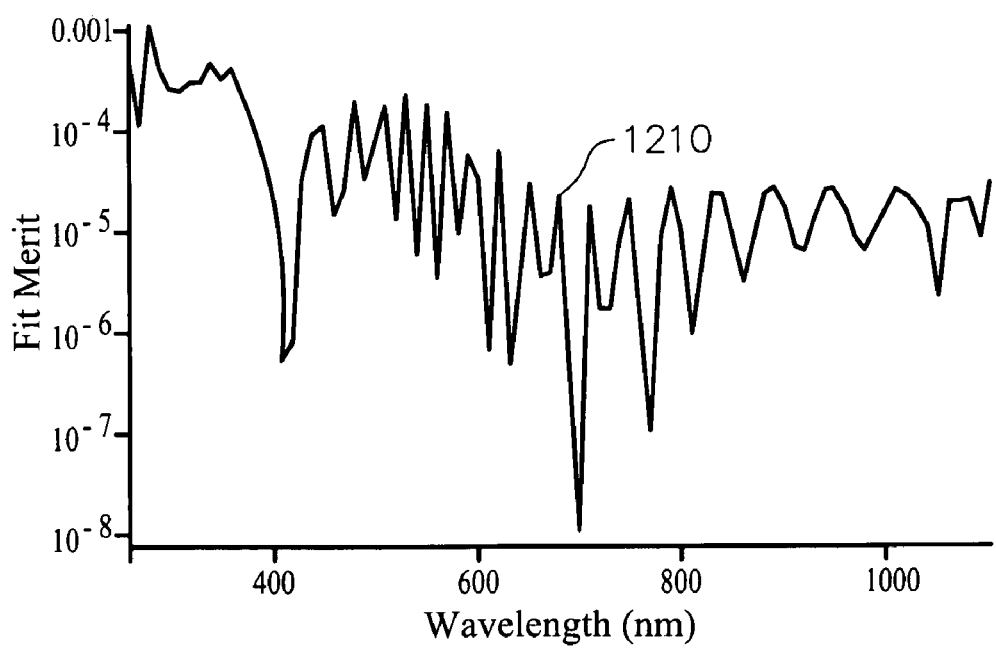
FIG. 12B is a fit merit plot for the results shown in FIG. 12A.

The Sellmeier coefficients for this example were: {0.00187037, {B1→0.829063, B2→0.599588, B3→1.38423, C1→0.0118092, C2→0.0292444, C3→115.424}}; where the first number is the value of the objective function (equation (16)) after fitting. The Sellmeier coefficients were used to compute the particle refractive index using the point-by-point objective function (equation (14)) to get a sense of how well the refractive index fits across the spectrum. The result 1210 of this calculation for 3 μm polystyrene particles is shown in FIG. 12B. The fit merit is computed by plotting the objective function (equation (14)) using the computed refractive index η at each wavelength to provide a measure of the fit quality at each point. A typical threshold fit value is set a $10^{-4}$, wherein a fit merit value less than or equal to about $10^{-4}$ indicates a good fit. It can be observed in FIG. 12B that the fit was reasonably good, except in the UV wavelengths at the short end of the spectrum.

A third method of calculating refractive indices is referred to as the point-by-point complex refractive index solver. This method provides a logical extension of the point-by-point refractive index solver from real refractive indices to complex refractive indices, for use with opaque materials. In this approach, two spectral measurements are required to solve for the complex refractive index, since the computation of two variables is required. Thus, the extinction spectra of two dilute colloids with different particle sizes are measured in order to compute the refractive index. The objective function that is minimized using this approach is sum of two functions of the form in equation (14), one for each spectrum.

Figure 13A:
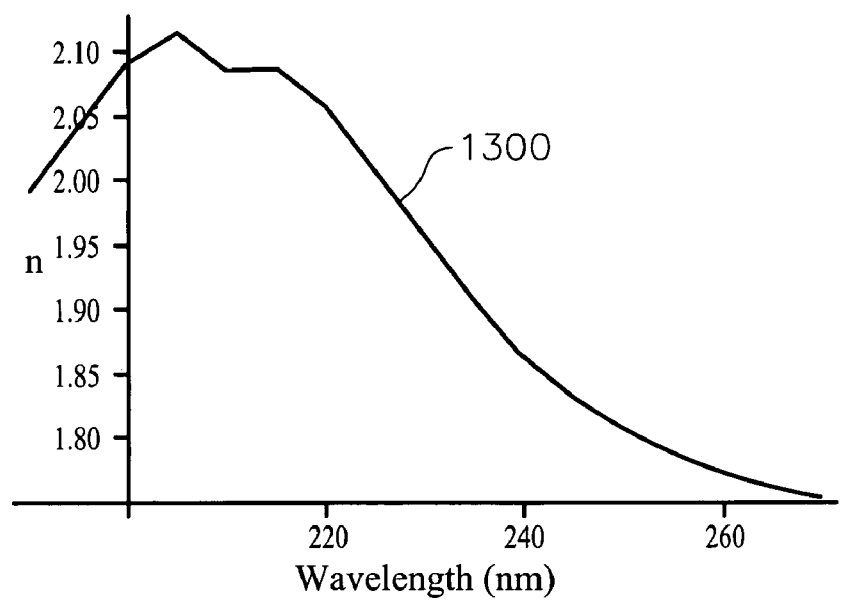
FIGS. 13A and 13B show real and imaginary refractive index plots, respectively, for polystyrene particles.
Figure 13B:
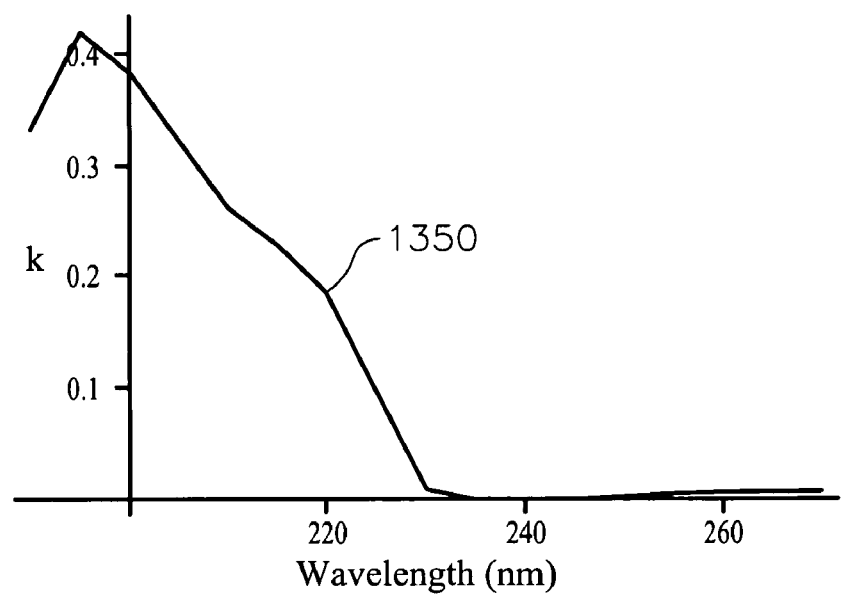

FIGS. 13A and 13B show the real and imaginary refractive index plots 1300 and 1350, respectively, for polystyrene particles. The first measured spectrum was measured from a monodisperse colloid of 74 nm polystyrene particles and the second measured spectrum was measured from a monodisperse colloid of 155 nm polystyrene particles. The point-by-point refractive index solver method was used for the real part calculations at wavelengths greater than about 270 nm. For shorter wavelengths, the point-by-point complex refractive index solver method was used, with a starting refractive index guess with k=0 and n=the 280 nm real refractive index resulting from the real refractive index solution provided by the point-by-point refractive index solver method The term "k" is defined as the imaginary component of the refractive index, and "n" is the real component of the refractive index, which can be written as ñ=n+ik, where i is the square root of −1. The tilde above the n on the left side of the equation means the n is a complex number, a fairly common notation. Starting at 270 nm, incremental changes in n of +/−0.05 and in k of +/−0.1 were allowed in each of the 5 nm wavelength increments. This method requires that the initial n and k assignments be positive numbers.

In examining the fit merit for these results, it was found that the fit was good everywhere except near 230 nm. It was postulated that the bad fit results near 230 nm may have been caused by some contamination in the sample(s).

Figure 14:
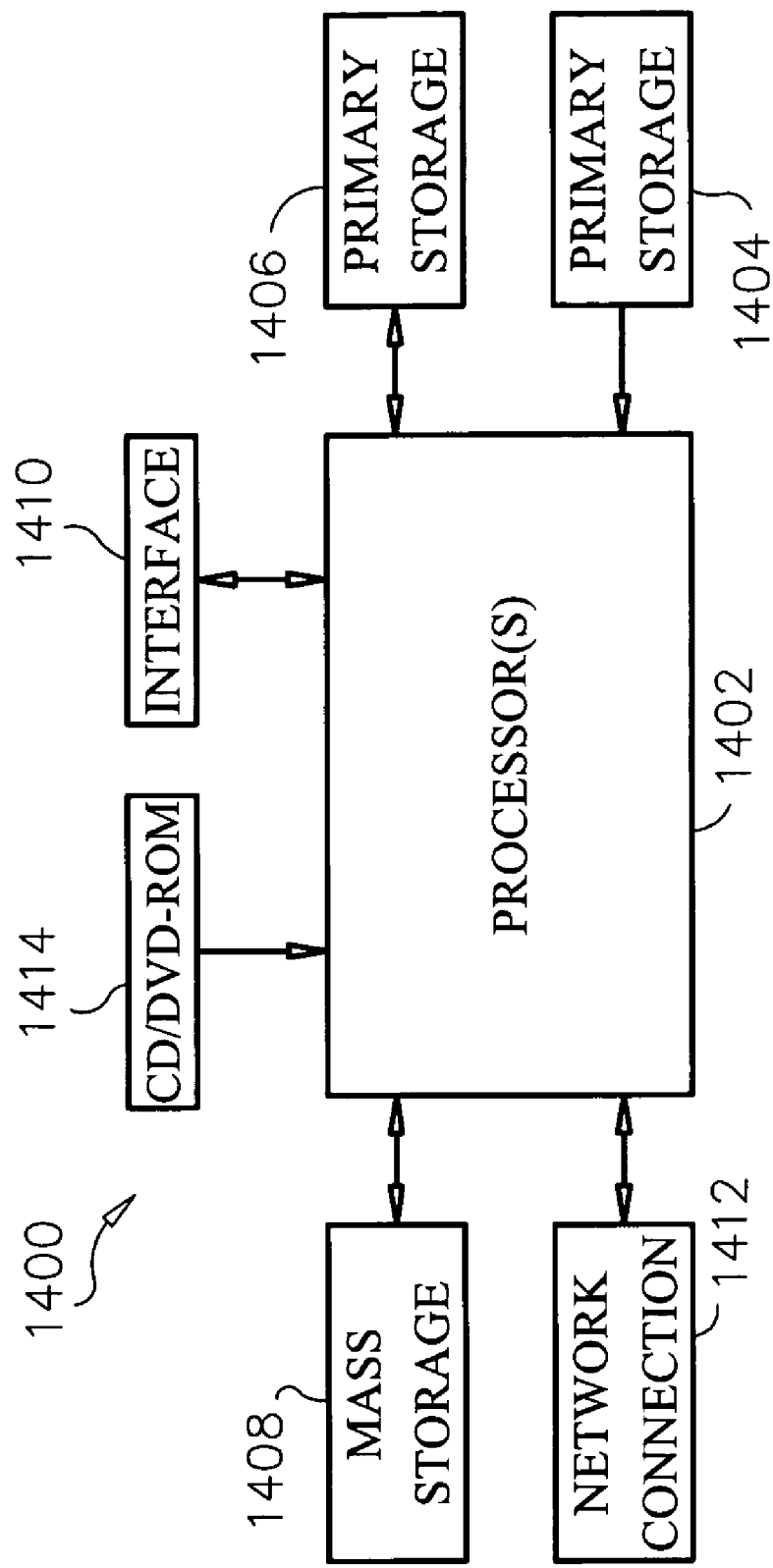
FIG. 14 illustrates a typical computer system in accordance with an embodiment of the present invention.

FIG. 14 illustrates a typical computer system 1400 in accordance with an embodiment of the present invention. The computer system 1400 may be incorporated into a spectrophotometer system, or may be configured to receive spectrophotometric data from a spectrophotometer via interface 1410, for example, and with user interaction via interface 1410 of the system 1400, such as in conjunction with user interface 260. Computer system 1400 includes any number of processors 1402 (also referred to as central processing units, or CPUs) that are coupled to storage devices including primary storage 1406 (typically a random access memory, or RAM), primary storage 1404 (typically a read only memory, or ROM). Primary storage 1404 acts to transfer data and instructions uni-directionally to the CPU and primary storage 1406 is used typically to transfer data and instructions in a bi-directional manner. Both of these primary storage devices may include any suitable computer-readable media such as those described above. A mass storage device 1408 is also coupled bi-directionally to CPU 1402 and provides additional data storage capacity and may include any of the computer-readable media described above. Mass storage device 1408 may be used to store programs, such as PSD calculation programs, refractive index calculation programs, post processing programs, and the like and is typically a secondary storage medium such as a hard disk that is slower than primary storage. It will be appreciated that the information from primary storage 1406, may, in appropriate cases, be stored on mass storage device 1408 as virtual memory to free up space on primary storage 1406, thereby increasing the effective memory of primary storage 1406. A specific mass storage device such as a CD-ROM or DVD-ROM 1414 may also pass data uni-directionally to the CPU.

CPU 1402 is also coupled to an interface 1410 that includes one or more input/output devices such as video monitors, user interface, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 1402 optionally may be coupled to a computer or telecommunications network using a network connection as shown generally at 1412. With such a network connection, it is contemplated that the CPU might receive information from the network, or might output information to the network in the course of performing the above-described methods. The above-described devices and materials are known in the computer hardware and software arts.

The hardware elements described above may operate in response to the instructions of multiple software modules for performing the operations of this invention. For example, instructions for calculating particle size distributions and concentrations and instructions for post processing may be stored on mass storage device 1408 or 1414 and executed on CPU 1408 in conjunction with primary memory 1406.

While the present invention has been described with reference to the specific embodiments thereof, it should be understood that various changes may be made and equivalents may be substituted without departing from the scope of the invention.

We claim:

1. A method for computing small particle size distributions, comprising:
    providing a reference matrix of pre-computed or pre-measured reference vectors, each reference vector representing a discrete particle size of a particle size distribution of particles contained in a dilute colloid, each reference vector representing a reference extinction spectrum over a predetermined wavelength range;
    providing a measurement vector representing a measured extinction spectrum of the sample particles in the sample colloid, wherein the measured extinction spectrum has been spectrophotometrically measured;
    determining at least one of a particle size, the particle size distribution and at least one particle concentration of the particles in the sample dilute colloid, using the reference matrix, the measurement vector and linear equations; and
    smoothing results calculated for the determining at least one of a particle size, the particle size distribution and at least one particle concentration of the particles in the sample dilute colloid.

2. The method of claim 1, wherein each reference vector includes pairs of wavelength and extinction values measured over predetermined wavelengths spectrophotometrically.

3. The method of claim 1, wherein said determining comprises applying a non-negative least squares algorithm to the reference matrix and the measurement vector to solve for the particle size distribution and particle concentrations of the sample particles.

4. The method of claim 1, wherein particle sizes of the particles in the sample dilute colloid are in the range of about 10 nm to about 15 μm.

5. The method of claim 1, wherein the reference extinction spectra comprise extinction values determined from Mie scattering spectra.

6. The method of claim 1, wherein the wavelength range is from about 190 nm to about 1100 nm.

7. The method of claim 1, wherein said determining comprises:
    calculating a least squares error between the reference matrix and the measurement vector; and
    finding a concentration vector that minimizes the least squares error, wherein the concentration vector represents the particle concentrations of the particles in the sample dilute colloid.

8. The method of claim 1, wherein said determining includes iteratively removing from the reference matrix at least one of the reference vectors that represents a largest discrete particle size and each time determining the particle size distribution and concentrations of particles in the sample dilute colloid until an error in a fit of the measurement vector to the reference matrix that is greater than a predetermined error tolerance is calculated.

9. The method of claim 1, further comprising:
compensating for forward scattering effects by applying a forward scattering correction factor to values of the reference matrix.

10. The method of claim 1, further comprising:
outputting at least one of the at least one of a particle size, the particle size distribution and at least one particle concentration of the particles in the sample dilute colloid for use by a user.

11. A method for computing at least one of small particle size and small particle concentration, said method comprising:
providing a reference matrix of pre-computed or pre-measured reference vectors, each reference vector representing a discrete particle size of a particle size distribution of particles contained in a dilute colloid, each the reference vector including a reference extinction spectrum over a predetermined wavelength range;
providing a measurement vector representing a measured extinction spectrum of the sample particles in the sample colloid, wherein the measured extinction spectrum has been spectrophotometrically measured;
determining the particle size distribution in the sample dilute colloid, using linear equations, the reference matrix and the reference vector;
determining whether the determined particle size distribution is a broad distribution, based on a predetermined percentage of non-zero particle size values in the particle size distribution;
when the determined particle size distribution is not a broad distribution, finding a best fit solution from the determined particle size distribution and particle concentrations relative to the matrix; and
when the determined particle size distribution is a broad distribution, iteratively removing from the reference matrix at least one of the pre-computed reference vectors that represents a largest discrete particle size and each time determining the particle size distribution and particle concentrations in the sample dilute colloid until an error in a fit of the measurement vector to the reference matrix that is greater than a predetermined error tolerance is calculated, and finding a best fit solution from the determined particle size distribution and particle concentrations relative to the matrix after the iteratively removing.

12. The method of claim 11, wherein each said reference vector includes pairs of wavelength and extinction values measured over discrete wavelengths spectrophotometrically.

13. The method of claim 11, wherein said best fit solution when the determined particle size distribution is not a broad distribution is a solution produced by one of: smoothing the determined particle size distribution and particle concentrations, selecting a single match size from the determined particle size distribution that best matches the measurement vector, and selecting a single match size from the determined particle size distribution that best matches the measurement vector and smoothing the best single match.

14. The method of claim 13, wherein said smoothing comprises Gaussian blurring.

15. The method of claim 11, further comprising smoothing said best fit solution when the determined particle size distribution is a broad distribution.

16. The method of claim 15, wherein said smoothing comprises Gaussian blurring.

17. The method of claim 11, wherein the provision of the measurement vector comprises:
measuring by spectrophotometry the measurement vector, wherein the extinction values are measured at discrete wavelengths.

18. A system for measuring at least one of small particle size and small particle concentration, said system comprising:
a processor;
a reference matrix of pre-computed or pre-measured reference vectors stored in memory that is accessible by the processor, each reference vector representing a discrete particle size of a particle size distribution of particles contained in a dilute colloid, each the reference vector including a reference extinction spectrum over a predetermined wavelength range; and
programming configured to be run by the processor, when the system is provided with a measurement vector representing a measured extinction spectrum of the sample particles in the sample colloid, wherein the measured extinction spectrum has been spectrophotometrically measured, to cause the processor to perform operations comprising:
determining at least one of a particle size, the particle size distribution, and at least one particle concentration of the particles in the sample colloid, using linear equations, the reference matrix and the reference vector; and
smoothing results calculated for the determining at least one of a particle size, the particle size distribution and at least one particle concentration of the particles in the sample dilute colloid.

19. The system of claim 18, wherein each said reference vector includes pairs of wavelength and scattering values measured over discrete wavelengths spectrophotometrically.

20. The system of claim 18, further comprising programming configured to be run by the processor to pre-compute the reference matrix of pre-computed reference vectors.

21. The system of claim 18, further comprising:
a spectrophotometer configured to measure the extinction values of the sample particles in the sample colloid, the spectrophotometer further being configured to perform at least one of calculating and inputting the measurement vector of the extinction values, and inputting the extinction values of the sample particles in the sample colloid to the processor.

22. The system of claim 18, wherein said programming is configured to determine the particle size distribution and particle concentrations in the sample dilute colloid by applying a non-negative least squares algorithm to solve for the particle size distribution and particle concentrations in the sample dilute colloid, using the reference matrix and the measurement vector as inputs.

23. The system of claim 18, wherein said discrete wavelengths are within a range of wavelengths from about 190 nm to about 1100 nm.

24. The system of claim 18, wherein said processor executes the programming to calculate a least squares error between the reference matrix and the measurement vector, and find a concentration vector that minimizes the least squares error.

25. The system of claim 18, wherein said processor executes programming to compensate for forward scattering effects by applying a forward scattering correction factor to values of the reference matrix.

26. A computer readable medium carrying one or more sequences of instructions for computing at least one of small particle size and small particle concentration is provided, wherein execution of the one or more sequences of instructions by one or more processors causes the one or more processors to perform a process comprising:

receiving a reference matrix of pre-computed or pre-measured reference vectors, each reference vector representing a discrete particle size of a particle size distribution of particles in a dilute colloid, each the reference vector representing a reference extinction spectrum over a predetermined wavelength range;

receiving a measurement vector representing a measured extinction spectrum of the sample particles in the sample colloid, wherein the measured extinction spectrum has been spectrophotometrically measured;

determining at least one of a particle size, the particle size distribution and at least one particle concentration of the particles in the sample dilute colloid, using the reference matrix, the measurement vector and linear equations; and smoothing results calculated for the determining at least one of a particle size, the particle size distribution and at least one particle concentration of the particles in the sample dilute colloid.

27. The computer readable medium of claim 26, wherein each said reference vector includes pairs of wavelength and extinction values measured over discrete wavelengths spectrophotometrically.

* * * * *